United States Patent
Taylor et al.

(10) Patent No.: US 9,814,612 B2
(45) Date of Patent: Nov. 14, 2017

(54) STENT-GRAFT WITH POSITIONING ANCHOR

(71) Applicant: NELLIX, INC., Irvine, CA (US)

(72) Inventors: Charles S. Taylor, San Francisco, CA (US); Christopher Zarins, Portola Valley, CA (US); Robert A. Geshlider, San Francisco, CA (US); Dwight P. Morejohn, Davis, CA (US); Peter Johansson, Lafayette, CA (US); Susan W. Vican, San Francisco, CA (US); James T. McKinley, Woodside, CA (US)

(73) Assignee: Nellix, Inc., Irvine, CA (US)

( * ) Notice: Subject to any disclaimer, the term of this patent is extended or adjusted under 35 U.S.C. 154(b) by 0 days.

(21) Appl. No.: 14/697,433

(22) Filed: Oct. 21, 2015

(65) Prior Publication Data
US 2016/0030215 A1 Feb. 4, 2016

Related U.S. Application Data

(62) Division of application No. 11/876,458, filed on Oct. 22, 2007, now Pat. No. 9,113,999, which is a division
(Continued)

(51) Int. Cl.
*A61F 2/954* (2013.01)
*A61F 2/958* (2013.01)
(Continued)

(52) U.S. Cl.
CPC ............... *A61F 2/958* (2013.01); *A61F 2/07* (2013.01); *A61F 2002/061* (2013.01);
(Continued)

(58) Field of Classification Search
CPC .... A61F 2002/077; A61F 2/954; A61F 2/958; A61M 2025/1013; A61M 2025/1059; A61B 2017/22068
See application file for complete search history.

(56) References Cited

U.S. PATENT DOCUMENTS

| 4,565,738 A | 1/1986 | Purdy |
| 4,638,803 A | 1/1987 | Rand |

(Continued)

FOREIGN PATENT DOCUMENTS

| DE | 4010975 A1 | 10/1991 |
| EP | 0679372 A2 | 11/1995 |

(Continued)

OTHER PUBLICATIONS

Carmi et al., "Endovascular stent-graft adapted to the endoluminal environment: prototype of a new endoluminal approach," J Endovasc Ther. Jun. 2002;9(3):380-381.
(Continued)

*Primary Examiner* — Brian Pellegrino
(74) *Attorney, Agent, or Firm* — Kilpatrick, Townsend & Stockton, LLP

(57) ABSTRACT

A positioning anchor is provided for a stent-graft for implantation to treat a damaged body lumen. The positioning anchor is generally tubular surrounding a primary fluid conduit. Arms extend laterally from the generally tubular structure of the anchor surrounding lateral fluid conduits. The form of these arms is preferably custom configured to match a particular patient's luminal geometry. The anchor thus fits within the luminal geometry to remain in a desired fixed position for implantation of the anchor and any stent-graft coupled to the anchor. The anchor is most preferably formed with two walls having a void therebetween which can be filled with fixation media to further secure the anchor at the desired implantation site. A lumen shaper balloon and
(Continued)

delivery catheter are also disclosed for proper delivery, expansion and inflation of the positioning anchor and stent-graft elements according to this invention.

15 Claims, 12 Drawing Sheets

Related U.S. Application Data of application No. 10/668,901, filed on Sep. 22, 2003, now abandoned.

(60) Provisional application No. 60/412,501, filed on Sep. 20, 2002.

(51) Int. Cl.
  *A61F 2/07* (2013.01)
  *A61F 2/06* (2013.01)

(52) U.S. Cl.
  CPC ... *A61F 2002/065* (2013.01); *A61F 2002/077* (2013.01); *A61F 2230/0069* (2013.01); *A61F 2240/002* (2013.01); *A61F 2250/0003* (2013.01)

(56) References Cited

U.S. PATENT DOCUMENTS

| | | |
|---|---|---|
| 4,641,653 A | 2/1987 | Rockey |
| 4,704,126 A | 11/1987 | Baswell |
| 4,710,192 A | 12/1987 | Liotta |
| 4,728,328 A | 3/1988 | Hughes |
| 4,731,073 A | 3/1988 | Robinson |
| 4,733,665 A | 3/1988 | Palmaz |
| 4,743,258 A | 5/1988 | Ikada |
| 4,763,654 A | 8/1988 | Jang |
| 4,856,516 A | 8/1989 | Hillstead |
| 4,858,264 A | 8/1989 | Reinhart |
| 4,892,544 A | 1/1990 | Frisch |
| 4,976,692 A | 12/1990 | Atad |
| 5,002,532 A | 3/1991 | Gaiser |
| 5,074,845 A | 12/1991 | Miraki |
| 5,104,404 A | 4/1992 | Wolff |
| 5,108,417 A | 4/1992 | Sawyer |
| 5,122,154 A | 6/1992 | Rhodes |
| 5,133,732 A | 7/1992 | Wiktor |
| 5,139,480 A | 8/1992 | Hickle |
| 5,156,620 A | 10/1992 | Pigott |
| 5,195,984 A | 3/1993 | Schatz |
| 5,217,484 A | 6/1993 | Marks |
| 5,222,970 A | 6/1993 | Reeves |
| 5,234,437 A | 8/1993 | Sepetka |
| 5,242,399 A | 9/1993 | Lau |
| 5,250,071 A | 10/1993 | Palermo |
| 5,261,916 A | 11/1993 | Engelson |
| 5,263,964 A | 11/1993 | Purdy |
| 5,292,331 A | 3/1994 | Boneau |
| 5,314,444 A | 5/1994 | Gianturco |
| 5,316,023 A | 5/1994 | Palmaz |
| 5,330,528 A | 7/1994 | Lazim |
| 5,334,024 A | 8/1994 | Niznick |
| 5,334,217 A | 8/1994 | Das |
| 5,350,397 A | 9/1994 | Palermo |
| 5,352,199 A | 10/1994 | Tower |
| 5,375,612 A | 12/1994 | Cottenceau |
| 5,383,892 A | 1/1995 | Cardon |
| 5,421,955 A | 6/1995 | Lau |
| 5,423,849 A | 6/1995 | Engelson |
| 5,425,739 A | 6/1995 | Jessen |
| 5,425,744 A | 6/1995 | Fagan |
| 5,441,510 A | 8/1995 | Simpson |
| 5,441,515 A | 8/1995 | Khosravi |
| 5,443,477 A | 8/1995 | Marin |
| 5,443,496 A | 8/1995 | Schwartz |
| 5,449,373 A | 9/1995 | Pinchasik |
| 5,485,667 A | 1/1996 | Kleshinski |
| 5,494,029 A | 2/1996 | Lane |
| 5,496,277 A | 3/1996 | Termin |
| 5,507,767 A | 4/1996 | Maeda |
| 5,507,769 A | 4/1996 | Marin |
| 5,507,771 A | 4/1996 | Gianturco |
| 5,514,115 A | 5/1996 | Frantzen |
| 5,514,154 A | 5/1996 | Lau |
| 5,522,882 A | 6/1996 | Gaterud |
| 5,531,741 A | 7/1996 | Barbacci |
| 5,534,024 A | 7/1996 | Rogers et al. |
| 5,545,210 A | 8/1996 | Hess |
| 5,549,662 A | 8/1996 | Fordenbacher |
| 5,549,663 A | 8/1996 | Cottone, Jr. |
| 5,554,181 A | 9/1996 | Das |
| 5,562,641 A | 10/1996 | Flomenblit |
| 5,562,698 A | 10/1996 | Parker |
| 5,562,728 A | 10/1996 | Lazarus |
| 5,569,295 A | 10/1996 | Lam |
| 5,578,074 A | 11/1996 | Mirigian |
| 5,578,149 A | 11/1996 | De Scheerder |
| 5,591,195 A | 1/1997 | Taheri |
| 5,591,223 A | 1/1997 | Lock |
| 5,591,226 A | 1/1997 | Trerotola |
| 5,591,228 A | 1/1997 | Edoga |
| 5,591,230 A | 1/1997 | Horn |
| 5,593,417 A | 1/1997 | Rhodes |
| 5,601,600 A | 2/1997 | Ton |
| 5,603,721 A | 2/1997 | Lau |
| 5,605,530 A | 2/1997 | Fischell |
| 5,607,442 A | 3/1997 | Fischell |
| 5,607,445 A | 3/1997 | Summers |
| 5,607,468 A | 3/1997 | Rogers |
| 5,609,605 A | 3/1997 | Marshall |
| 5,617,878 A | 4/1997 | Taheri |
| 5,618,299 A | 4/1997 | Khosravi |
| 5,624,411 A | 4/1997 | Tuch |
| 5,630,840 A | 5/1997 | Mayer |
| 5,632,760 A | 5/1997 | Sheiban |
| 5,632,762 A | 5/1997 | Myler |
| 5,632,763 A | 5/1997 | Glastra |
| 5,632,771 A | 5/1997 | Boatman |
| D380,266 S | 6/1997 | Boatman |
| 5,634,941 A | 6/1997 | Winston |
| 5,636,641 A | 6/1997 | Fariabi |
| D380,831 S | 7/1997 | Kavteladze |
| 5,662,614 A | 9/1997 | Edoga |
| 5,665,117 A | 9/1997 | Rhodes |
| 5,674,241 A | 10/1997 | Bley |
| 5,676,697 A | 10/1997 | McDonald |
| 5,683,449 A | 11/1997 | Marcade |
| 5,690,643 A | 11/1997 | WiJay |
| 5,693,038 A | 12/1997 | Suzuki et al. |
| 5,693,067 A | 12/1997 | Purdy |
| 5,693,088 A | 12/1997 | Lazarus |
| 5,697,971 A | 12/1997 | Fischell |
| 5,709,707 A | 1/1998 | Lock |
| 5,718,713 A | 2/1998 | Frantzen |
| 5,723,004 A | 3/1998 | Dereume |
| 5,725,568 A | 3/1998 | Hastings |
| 5,725,572 A | 3/1998 | Lam |
| 5,728,068 A | 3/1998 | Leone |
| 5,728,131 A | 3/1998 | Frantzen |
| 5,728,158 A | 3/1998 | Lau |
| 5,733,303 A | 3/1998 | Israel et al. |
| 5,735,892 A | 4/1998 | Myers |
| 5,735,893 A | 4/1998 | Lau |
| 5,741,327 A | 4/1998 | Frantzen |
| 5,741,333 A | 4/1998 | Frid |
| 5,746,691 A | 5/1998 | Frantzen |
| 5,755,769 A | 5/1998 | Richard |
| 5,755,773 A | 5/1998 | Evans et al. |
| 5,755,778 A | 5/1998 | Kleshinski |
| 5,766,151 A | 6/1998 | Valley et al. |
| 5,766,238 A | 6/1998 | Lau |
| 5,769,882 A | 6/1998 | Fogarty et al. |
| 5,776,114 A | 7/1998 | Frantzen |
| 5,776,161 A | 7/1998 | Globerman |

(56) References Cited

U.S. PATENT DOCUMENTS

| | | |
|---|---|---|
| 5,782,907 A | 7/1998 | Frantzen |
| 5,785,679 A | 7/1998 | Abolfathi et al. |
| 5,788,626 A | 8/1998 | Thompson |
| 5,797,953 A | 8/1998 | Tekulve |
| 5,800,393 A | 9/1998 | Sahota |
| 5,800,512 A | 9/1998 | Lentz et al. |
| 5,800,514 A | 9/1998 | Nunez |
| 5,800,525 A | 9/1998 | Bachinski |
| 5,807,404 A | 9/1998 | Richter |
| 5,810,872 A | 9/1998 | Kanesaka |
| 5,824,036 A | 10/1998 | Lauterjung |
| 5,824,037 A | 10/1998 | Fogarty et al. |
| 5,824,040 A | 10/1998 | Cox |
| 5,824,049 A | 10/1998 | Ragheb |
| 5,824,054 A | 10/1998 | Khosravi et al. |
| 5,824,056 A | 10/1998 | Rosenberg |
| 5,827,321 A | 10/1998 | Roubin |
| 5,836,966 A | 11/1998 | St. Germain |
| 5,843,160 A | 12/1998 | Rhodes |
| 5,843,175 A | 12/1998 | Frantzen |
| 5,846,246 A | 12/1998 | Dirks |
| 5,846,261 A | 12/1998 | Kotula |
| 5,849,037 A | 12/1998 | Frid |
| 5,860,998 A | 1/1999 | Robinson |
| 5,863,627 A | 1/1999 | Szycher |
| 5,867,762 A | 2/1999 | Rafferty et al. |
| 5,868,685 A | 2/1999 | Powell et al. |
| 5,868,708 A | 2/1999 | Hart |
| 5,868,782 A | 2/1999 | Frantzen |
| 5,871,537 A | 2/1999 | Holman |
| 5,873,907 A | 2/1999 | Frantzen |
| 5,876,448 A | 3/1999 | Thompson et al. |
| 5,879,381 A | 3/1999 | Moriuchi |
| 5,888,660 A | 3/1999 | Landoni et al. |
| 5,902,332 A | 5/1999 | Schatz |
| 5,919,224 A | 7/1999 | Thompson |
| 5,928,279 A | 7/1999 | Shannon et al. |
| 5,931,866 A | 8/1999 | Frantzen |
| 5,944,750 A | 8/1999 | Tanner |
| 5,947,991 A | 9/1999 | Cowan |
| 5,948,184 A | 9/1999 | Frantzen |
| 5,976,178 A | 11/1999 | Goldsteen et al. |
| 5,984,955 A | 11/1999 | Wisselink |
| 5,994,750 A | 11/1999 | Yagi |
| 6,007,573 A | 12/1999 | Wallace |
| 6,015,431 A | 1/2000 | Thornton |
| 6,022,359 A | 2/2000 | Frantzen |
| 6,033,434 A | 3/2000 | Borghi |
| 6,042,606 A | 3/2000 | Frantzen |
| 6,056,776 A | 5/2000 | Lau |
| 6,066,167 A | 5/2000 | Lau |
| 6,066,168 A | 5/2000 | Lau |
| 6,083,259 A | 7/2000 | Frantzen |
| 6,093,199 A | 7/2000 | Brown |
| 6,099,548 A | 8/2000 | Taheri |
| 6,110,198 A | 8/2000 | Fogarty et al. |
| 6,123,715 A | 9/2000 | Amplatz |
| 6,123,722 A | 9/2000 | Fogarty |
| 6,124,523 A | 9/2000 | Banas et al. |
| 6,132,457 A | 10/2000 | Chobotov |
| 6,152,144 A | 11/2000 | Lesh |
| 6,152,943 A | 11/2000 | Sawhney |
| 6,168,592 B1 | 1/2001 | Kupiecki et al. |
| 6,187,033 B1 | 2/2001 | Schmitt |
| 6,187,034 B1 | 2/2001 | Frantzen |
| 6,190,402 B1 | 2/2001 | Horton et al. |
| 6,190,406 B1 | 2/2001 | Duerig et al. |
| 6,193,745 B1 | 2/2001 | Fogarty et al. |
| 6,196,230 B1 | 3/2001 | Hall et al. |
| 6,203,732 B1 | 3/2001 | Clubb |
| 6,214,022 B1 | 4/2001 | Taylor et al. |
| 6,231,562 B1 | 5/2001 | Khosravi et al. |
| 6,235,050 B1 | 5/2001 | Quiachon et al. |
| 6,241,761 B1 | 6/2001 | Villafana |
| 6,254,633 B1 | 7/2001 | Pinchuk et al. |
| 6,261,305 B1 | 7/2001 | Marotta et al. |
| 6,280,466 B1 | 8/2001 | Kugler |
| 6,283,991 B1 | 9/2001 | Cox et al. |
| 6,290,722 B1 | 9/2001 | Wang |
| 6,290,731 B1 | 9/2001 | Solovay et al. |
| 6,293,960 B1 | 9/2001 | Ken |
| 6,296,603 B1 | 10/2001 | Turnlund et al. |
| 6,299,597 B1 | 10/2001 | Buscemi et al. |
| 6,299,604 B1 | 10/2001 | Ragheb |
| 6,312,462 B1 | 11/2001 | McDermott et al. |
| 6,312,463 B1 | 11/2001 | Rourke et al. |
| 6,325,816 B1 | 12/2001 | Fulton, III |
| 6,325,819 B1 | 12/2001 | Pavcnik et al. |
| 6,331,184 B1 | 12/2001 | Abrams |
| 6,331,191 B1 | 12/2001 | Chobotov |
| 6,334,869 B1 | 1/2002 | Leonhardt et al. |
| 6,344,056 B1 | 2/2002 | Dehdashtian |
| 6,375,675 B2 | 4/2002 | Dehdashtian et al. |
| 6,395,019 B2 | 5/2002 | Chobotov |
| 6,409,757 B1 | 6/2002 | Trout, III et al. |
| 6,432,131 B1 | 8/2002 | Ravenscroft |
| 6,451,047 B2 | 9/2002 | McCrea |
| 6,463,317 B1 | 10/2002 | Kucharczyk et al. |
| 6,506,204 B2 | 1/2003 | Mazzocchi |
| 6,527,799 B2 | 3/2003 | Shanley |
| 6,544,276 B1 | 4/2003 | Azizi |
| 6,547,804 B2 | 4/2003 | Porter et al. |
| 6,554,858 B2 | 4/2003 | Dereume et al. |
| 6,576,007 B2 | 6/2003 | Dehdashtian et al. |
| 6,579,301 B1 | 6/2003 | Bales |
| 6,592,614 B2 | 7/2003 | Lenker et al. |
| 6,613,037 B2 | 9/2003 | Khosravi et al. |
| 6,645,242 B1 | 11/2003 | Quinn |
| 6,656,214 B1 | 12/2003 | Fogarty et al. |
| 6,656,220 B1 | 12/2003 | Gomez et al. |
| 6,663,607 B2 | 12/2003 | Slaikeu et al. |
| 6,663,667 B2 | 12/2003 | Dehdashtian et al. |
| 6,679,300 B1 | 1/2004 | Sommer et al. |
| 6,682,546 B2 | 1/2004 | Amplatz |
| 6,692,486 B2 | 2/2004 | Jaafar et al. |
| 6,695,833 B1 | 2/2004 | Frantzen |
| 6,729,356 B1 | 5/2004 | Baker et al. |
| 6,730,119 B1 | 5/2004 | Smalling |
| 6,733,521 B2 | 5/2004 | Chobotov |
| 6,761,733 B2 | 7/2004 | Chobotov |
| 6,773,454 B2 | 8/2004 | Wholey et al. |
| 6,776,771 B2 | 8/2004 | Van Moorlegem et al. |
| 6,827,735 B2 | 12/2004 | Greenberg |
| 6,843,803 B2 | 1/2005 | Ryan et al. |
| 6,878,161 B2 | 4/2005 | Lenker |
| 6,878,164 B2 | 4/2005 | Kujawski |
| 6,887,268 B2 | 5/2005 | Butaric et al. |
| 6,918,926 B2 | 7/2005 | Letort |
| 6,945,989 B1 | 9/2005 | Betelia et al. |
| 6,958,051 B2 | 10/2005 | Hart et al. |
| 6,960,227 B2 | 11/2005 | Jones et al. |
| 6,964,667 B2 | 11/2005 | Shaolian et al. |
| 7,001,431 B2 | 2/2006 | Bao et al. |
| 7,022,100 B1 | 4/2006 | Aboul-Hosn et al. |
| 7,105,012 B2 | 9/2006 | Trout, III |
| 7,112,217 B1 | 9/2006 | Kugler |
| 7,122,052 B2 | 10/2006 | Greenhalgh |
| 7,131,991 B2 | 11/2006 | Zarins et al. |
| 7,147,661 B2 | 12/2006 | Chobotov et al. |
| 7,175,651 B2 | 2/2007 | Kerr |
| 7,229,472 B2 | 6/2007 | DePalma et al. |
| 7,314,483 B2 | 1/2008 | Landau et al. |
| 7,326,237 B2 | 2/2008 | DePalma et al. |
| 7,435,253 B1 | 10/2008 | Hartley et al. |
| 7,530,988 B2 | 5/2009 | Evans et al. |
| 7,666,220 B2 | 2/2010 | Evans et al. |
| 7,682,383 B2 | 3/2010 | Robin |
| 7,708,773 B2 | 5/2010 | Pinchuk et al. |
| 7,790,273 B2 | 9/2010 | Lee et al. |
| 7,828,838 B2 | 11/2010 | Bolduc et al. |
| 7,872,068 B2 | 1/2011 | Khosravi et al. |
| 7,951,448 B2 | 5/2011 | Lee et al. |
| 8,044,137 B2 | 10/2011 | Khosravi et al. |
| 8,048,145 B2 | 11/2011 | Evans et al. |

(56) References Cited

U.S. PATENT DOCUMENTS

| | | |
|---|---|---|
| 8,182,525 B2 | 5/2012 | Herbowy et al. |
| 8,906,084 B2 | 12/2014 | Evans et al. |
| 8,926,682 B2 | 1/2015 | Herbowy et al. |
| 8,945,199 B2 | 2/2015 | Ganpath et al. |
| 2001/0020184 A1 | 9/2001 | Dehdashtian et al. |
| 2001/0027337 A1 | 10/2001 | Di Caprio |
| 2001/0027338 A1 | 10/2001 | Greenberg |
| 2001/0044655 A1 | 11/2001 | Patnaik et al. |
| 2002/0019665 A1 | 2/2002 | Dehdashtian et al. |
| 2002/0026217 A1 | 2/2002 | Baker et al. |
| 2002/0045848 A1 | 4/2002 | Jaafar et al. |
| 2002/0045931 A1 | 4/2002 | Sogard et al. |
| 2002/0052643 A1 | 5/2002 | Wholey et al. |
| 2002/0077594 A1 | 6/2002 | Chien et al. |
| 2002/0151953 A1 | 10/2002 | Chobotov |
| 2002/0151956 A1 | 10/2002 | Chobotov |
| 2002/0151958 A1 | 10/2002 | Chuter |
| 2002/0156518 A1 | 10/2002 | Tehrani |
| 2002/0165521 A1 | 11/2002 | Cioanta et al. |
| 2002/0169497 A1 | 11/2002 | Wholey et al. |
| 2002/0183629 A1 | 12/2002 | Fitz |
| 2003/0004560 A1 | 1/2003 | Chobotov |
| 2003/0009132 A1 | 1/2003 | Schwartz et al. |
| 2003/0014075 A1 | 1/2003 | Rosenbluth et al. |
| 2003/0028209 A1 | 2/2003 | Teoh et al. |
| 2003/0036745 A1 | 2/2003 | Khosravi et al. |
| 2003/0051735 A1 | 3/2003 | Pavcnik et al. |
| 2003/0074056 A1 | 4/2003 | Killion et al. |
| 2003/0078647 A1 | 4/2003 | Vallana et al. |
| 2003/0093145 A1 | 5/2003 | Lawrence-Brown et al. |
| 2003/0109916 A1* | 6/2003 | Don Michael ........ A61F 2/958 623/1.11 |
| 2003/0130720 A1 | 7/2003 | DePalma et al. |
| 2003/0130725 A1 | 7/2003 | DePalma et al. |
| 2003/0135269 A1 | 7/2003 | Swanstrom |
| 2003/0204242 A1 | 10/2003 | Zarins et al. |
| 2003/0204249 A1 | 10/2003 | Letort |
| 2003/0216802 A1 | 11/2003 | Chobotov et al. |
| 2003/0225446 A1 | 12/2003 | Hartley |
| 2004/0016997 A1 | 1/2004 | Ushio |
| 2004/0044358 A1 | 3/2004 | Khosravi et al. |
| 2004/0082989 A1 | 4/2004 | Cook et al. |
| 2004/0091543 A1 | 5/2004 | Bell et al. |
| 2004/0098096 A1 | 5/2004 | Eton |
| 2004/0116997 A1 | 6/2004 | Taylor et al. |
| 2004/0147811 A1 | 7/2004 | Diederich et al. |
| 2004/0153025 A1 | 8/2004 | Seifert et al. |
| 2004/0167607 A1 | 8/2004 | Frantzen |
| 2004/0193245 A1 | 9/2004 | Deem et al. |
| 2004/0204755 A1 | 10/2004 | Robin |
| 2004/0215172 A1 | 10/2004 | Chu et al. |
| 2004/0215316 A1 | 10/2004 | Smalling |
| 2004/0220522 A1 | 11/2004 | Briscoe et al. |
| 2004/0243057 A1 | 12/2004 | Vinten-Johansen |
| 2005/0004660 A1 | 1/2005 | Rosenbluth et al. |
| 2005/0027238 A1 | 2/2005 | Fago et al. |
| 2005/0028484 A1 | 2/2005 | Littlewood |
| 2005/0065592 A1 | 3/2005 | Holzer |
| 2005/0090804 A1 | 4/2005 | Chobotov et al. |
| 2005/0096731 A1 | 5/2005 | Looi et al. |
| 2005/0215989 A1 | 9/2005 | Abboud et al. |
| 2005/0245891 A1 | 11/2005 | McCormick et al. |
| 2005/0251251 A1 | 11/2005 | Cribier |
| 2006/0015173 A1 | 1/2006 | Clifford et al. |
| 2006/0025853 A1 | 2/2006 | Evans et al. |
| 2006/0074481 A1 | 4/2006 | Vardi et al. |
| 2006/0135942 A1 | 6/2006 | Fernandes et al. |
| 2006/0142836 A1 | 6/2006 | Hartley et al. |
| 2006/0155369 A1 | 7/2006 | Edwin et al. |
| 2006/0161244 A1 | 7/2006 | Seguin |
| 2006/0184109 A1 | 8/2006 | Gobel |
| 2006/0206197 A1 | 9/2006 | Morsi |
| 2006/0222596 A1 | 10/2006 | Askari et al. |
| 2006/0265043 A1 | 11/2006 | Mandrusov et al. |
| 2006/0292206 A1 | 12/2006 | Kim et al. |
| 2007/0032850 A1 | 2/2007 | Ruiz et al. |
| 2007/0043420 A1 | 2/2007 | Lostetter |
| 2007/0050008 A1 | 3/2007 | Kim et al. |
| 2007/0055355 A1 | 3/2007 | Kim et al. |
| 2007/0061005 A1 | 3/2007 | Kim et al. |
| 2007/0150041 A1 | 6/2007 | Evans et al. |
| 2007/0162109 A1 | 7/2007 | Davila et al. |
| 2007/0208416 A1 | 9/2007 | Burpee et al. |
| 2007/0276477 A1 | 11/2007 | Lee et al. |
| 2008/0039923 A1 | 2/2008 | Taylor et al. |
| 2008/0154368 A1 | 6/2008 | Justis et al. |
| 2008/0228259 A1 | 9/2008 | Chu |
| 2008/0294237 A1 | 11/2008 | Chu |
| 2009/0099649 A1 | 4/2009 | Chobotov et al. |
| 2009/0209855 A1 | 8/2009 | Drilling et al. |
| 2009/0216125 A1 | 8/2009 | Lenker |
| 2009/0319029 A1 | 12/2009 | Evans et al. |
| 2010/0004728 A1 | 1/2010 | Rao et al. |
| 2010/0036360 A1 | 2/2010 | Herbowy et al. |
| 2010/0217383 A1 | 8/2010 | Leonhardt et al. |
| 2012/0046684 A1 | 2/2012 | Evans et al. |

FOREIGN PATENT DOCUMENTS

| | | |
|---|---|---|
| EP | 1325717 A2 | 7/2003 |
| EP | 1903985 | 4/2008 |
| FR | 2834199 A1 | 7/2003 |
| JP | H04-322665 A | 11/1992 |
| JP | 2003-525692 A | 9/2003 |
| JP | 2004-537353 A | 12/2004 |
| JP | 2005-505380 A | 2/2005 |
| JP | 2005-532120 A | 10/2005 |
| JP | 2008-510502 A | 4/2008 |
| WO | 97/17912 A1 | 5/1997 |
| WO | 97/19653 A1 | 6/1997 |
| WO | 98/53761 A1 | 12/1998 |
| WO | 99/00073 A1 | 1/1999 |
| WO | 99/44539 A2 | 9/1999 |
| WO | 00/29060 A2 | 5/2000 |
| WO | 00/51522 A1 | 9/2000 |
| WO | 01/21108 A1 | 3/2001 |
| WO | 01/66038 A2 | 9/2001 |
| WO | 02/078569 A2 | 10/2002 |
| WO | 02/083038 A2 | 10/2002 |
| WO | 02/102282 A1 | 12/2002 |
| WO | 03/007785 A2 | 1/2003 |
| WO | 03/032869 A1 | 4/2003 |
| WO | 03/037222 A2 | 5/2003 |
| WO | 03/053288 A1 | 7/2003 |
| WO | 2004/004603 A1 | 1/2004 |
| WO | 2004/026183 A1 | 4/2004 |
| WO | 2004/037116 A2 | 5/2004 |
| WO | 2004/045393 A2 | 6/2004 |
| WO | 2006/012567 A2 | 2/2006 |
| WO | 2006/116725 A2 | 11/2006 |
| WO | 2007008600 A2 | 1/2007 |
| WO | 2007/142916 A2 | 12/2007 |

OTHER PUBLICATIONS

Donayre et al., "Fillable Endovascular Aneurysm Repair," Endovascular Today, pp. 64-66, Jan. 2009.

Gilling-Smith, "Stent Graft Migration After Endovascular Aneurysm Repair," presented at 25th International Charing Cross Symposium, Apr. 13, 2003 [Power Point Presentation and Transcript], 56 pages total.

Journal of Endovascular Therapy; Apr. 2000; pp. 111, 114, 132-140; vol. 7' No. 2; International Society of Endovascular Specialists; Phoenix, AZ.

Patrick W. Serruys and Michael JB Kutryk; Handbook of Coronary Stents, Second Edition; 1998; pp. 45, 55, 78, 103, 112, 132, 158, 174, 185, 190, 207, 215, 230, 239; Martin Dunitz; UK.

Shan-e-ali Haider et al. Sac behavior after aneurysm treatment with the Gore Excluder low-permeability aortic endoprosthesis: 12-month comparison to the original Excluder device. Journal of Vascular Surgery. vol. 44, No. 4. 694-700. Oct. 2006.

(56) References Cited

OTHER PUBLICATIONS

Susan M. Trocciola et al. The development of endotension is associated with increased transmission of pressure and serous components in porous expanded polytetrafluoroethylene stent-grafts: Characterization using a canine model. Journal of Vascular Surgery. Jan. 2006. pp. 109-116.
William Tanski, Mark Fillinger. Outcomes of original and low-permeability Gore Excluder endoprosthesis for endovascular abdominal aortic aneurysm repair. Journal of Vascular Surgery. Feb. 2007. p. 243-249.
U.S. Appl. No. 60/855,889, filed Oct. 31, 2006; first named inventor: Steven L. Herbowy.
U.S. Appl. No. 61/052,059, filed May 9, 2008; first named inventor: Gwendolyn A. Watanabe.
Examination Report of European Application No. 03754880.7, dated Dec. 16, 2010, 5 pages.
Examination Report of European Application No. 03754880.7, dated Dec. 22, 2011, 4 pages.
Examination Report of European Application No. 03754880.7, dated Jun. 29, 2012, 4 pages.
Examination Report of European Application No. 03754880.7, dated Feb. 22, 2013, 4 pages.
Examination Report of Japanese Patent Application No. 2011-506487, dated Jun. 11, 2013, 7 pages.
Examination report of European Application No. 09733719.0 dated Nov. 7, 2013, 6 pages.
Examination report of European Application No. 06751879.5, dated Mar. 24, 2014, 5 pages.
Examination Report of Japanese Patent Application No. 2011-506487, dated May 7, 2014, 7 pages.

\* cited by examiner

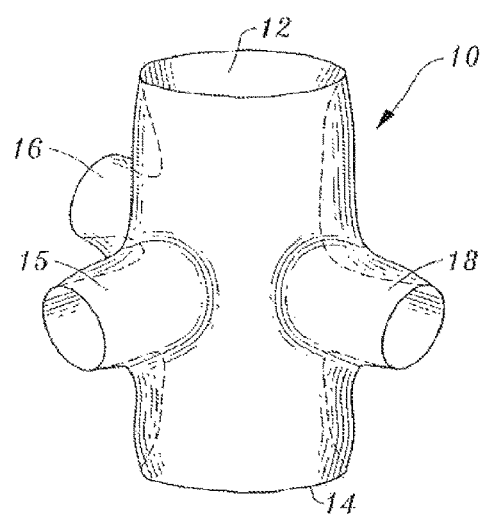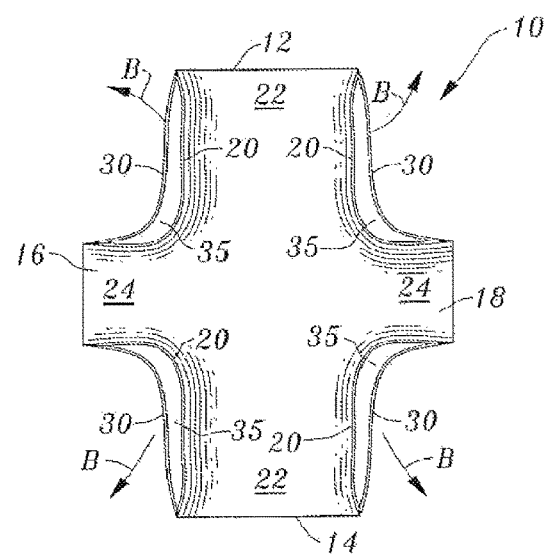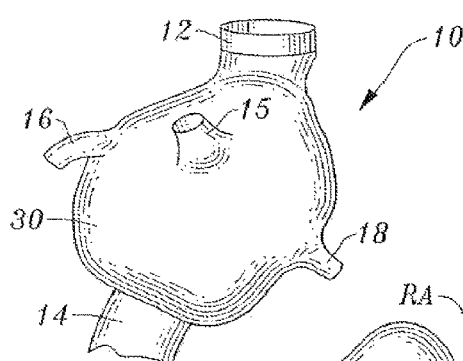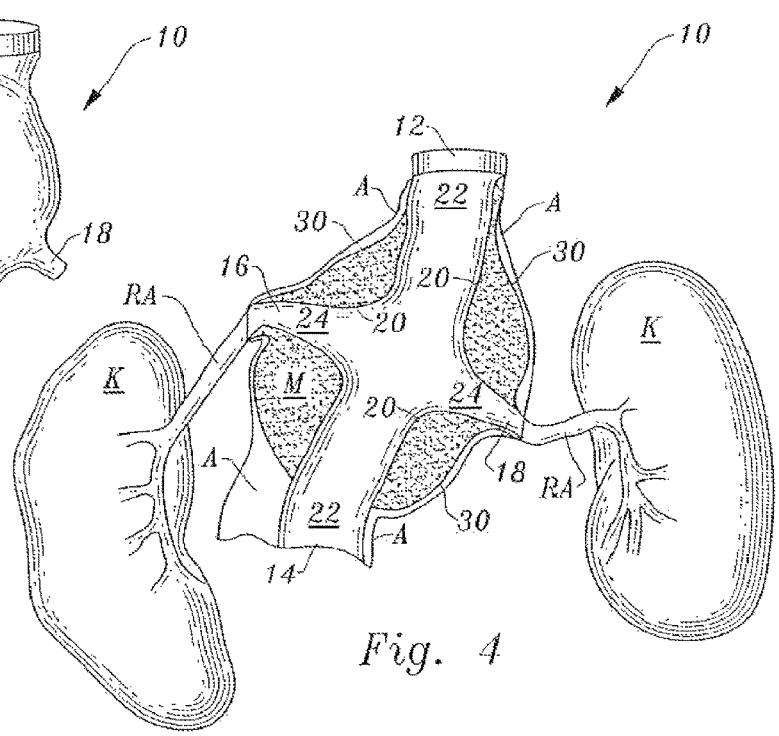
Fig. 1
Fig. 2
Fig. 3
Fig. 4

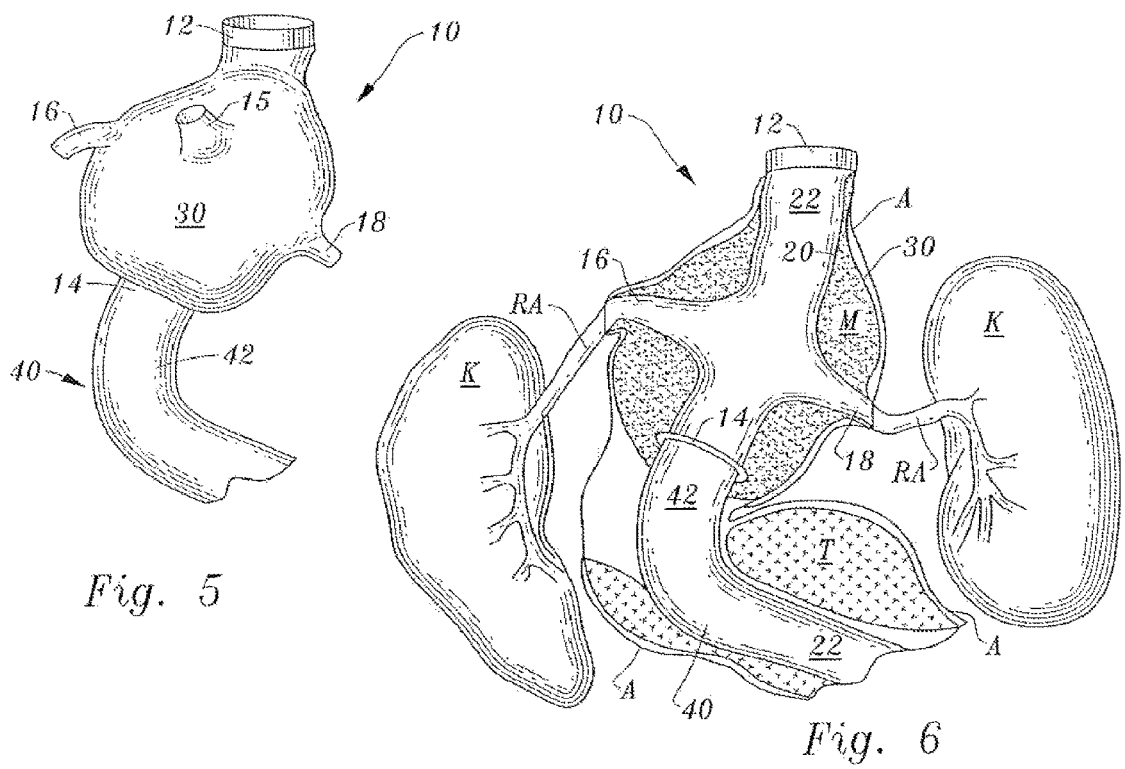
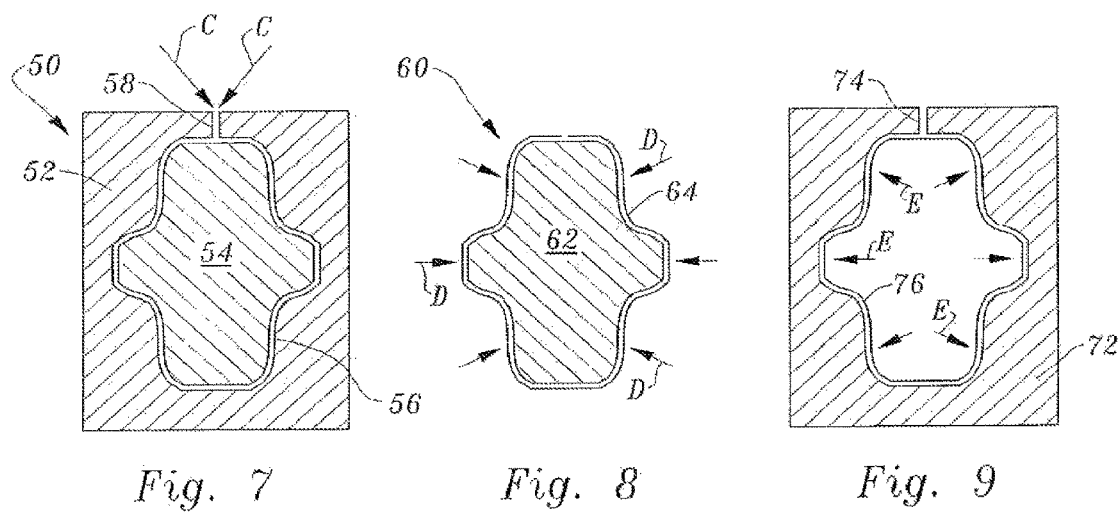
Fig. 5  Fig. 6
Fig. 7  Fig. 8  Fig. 9

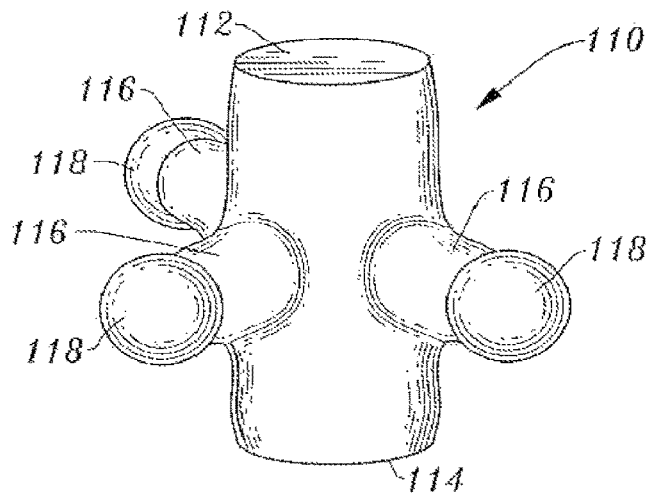

Fig. 25

| |
|---|
| The patient's X-ray, CT or Ultrasound data is converted to a CAD data file. |
| The CAD data is used to build 3D virtual models of both the shaper and the inner portion of the anchor. These virtual models digitally describe what will be used as a mandrel to form the actual devices. |
| The new CAD models are sent to a RP Machine. |
| The RP machine creates actual-sized 3D models of anchor and shaper. |
| The actual 3D model is used directly as a mandrel, or used to make other molds for balloon forming. |
| Form shaper or anchor upon mandrel or mold. |
| Dissolve or otherwise remove mandrel. |
| Install shaper and anchor on catheter/deployment device. |

Fig. 26

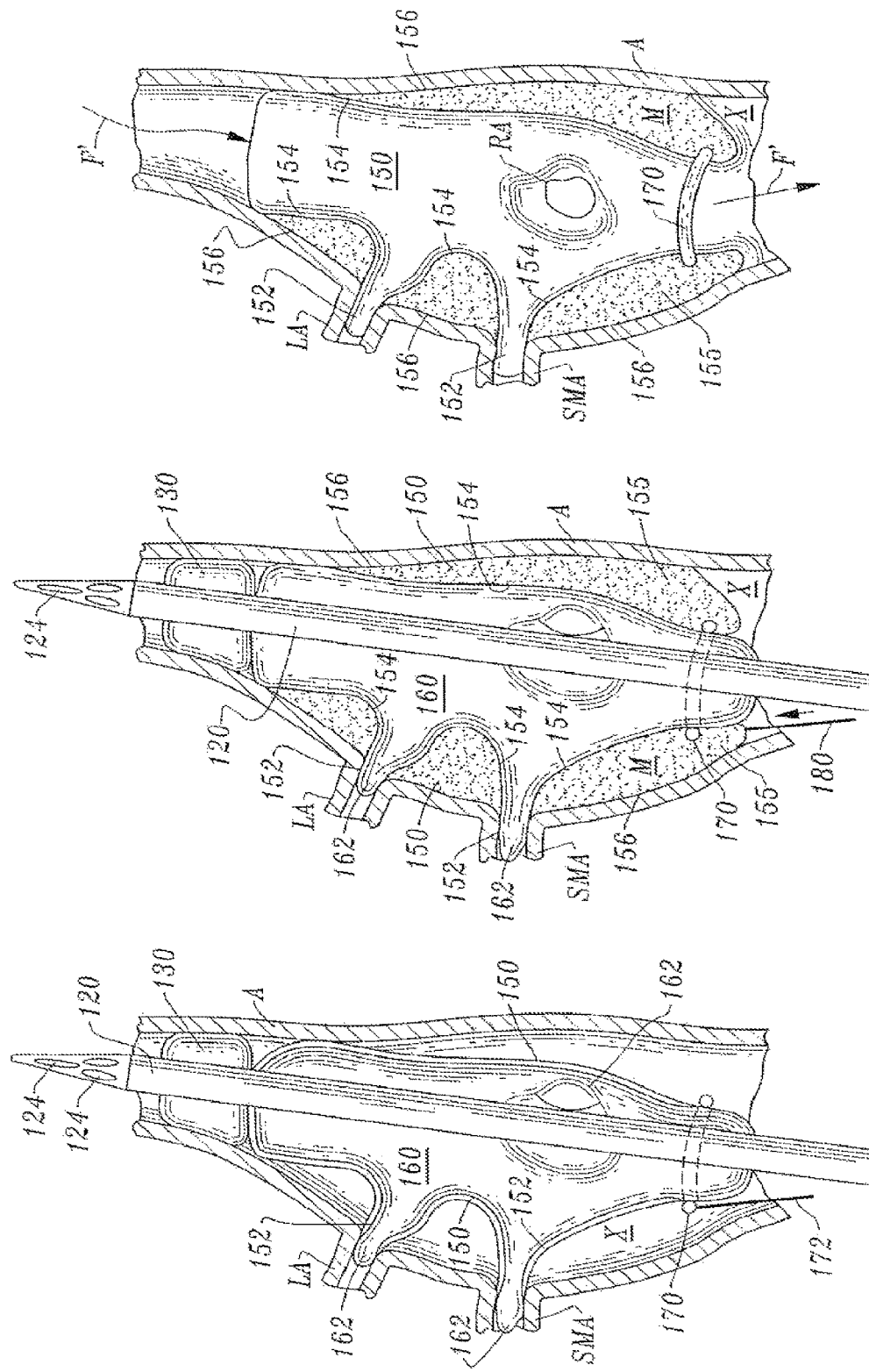

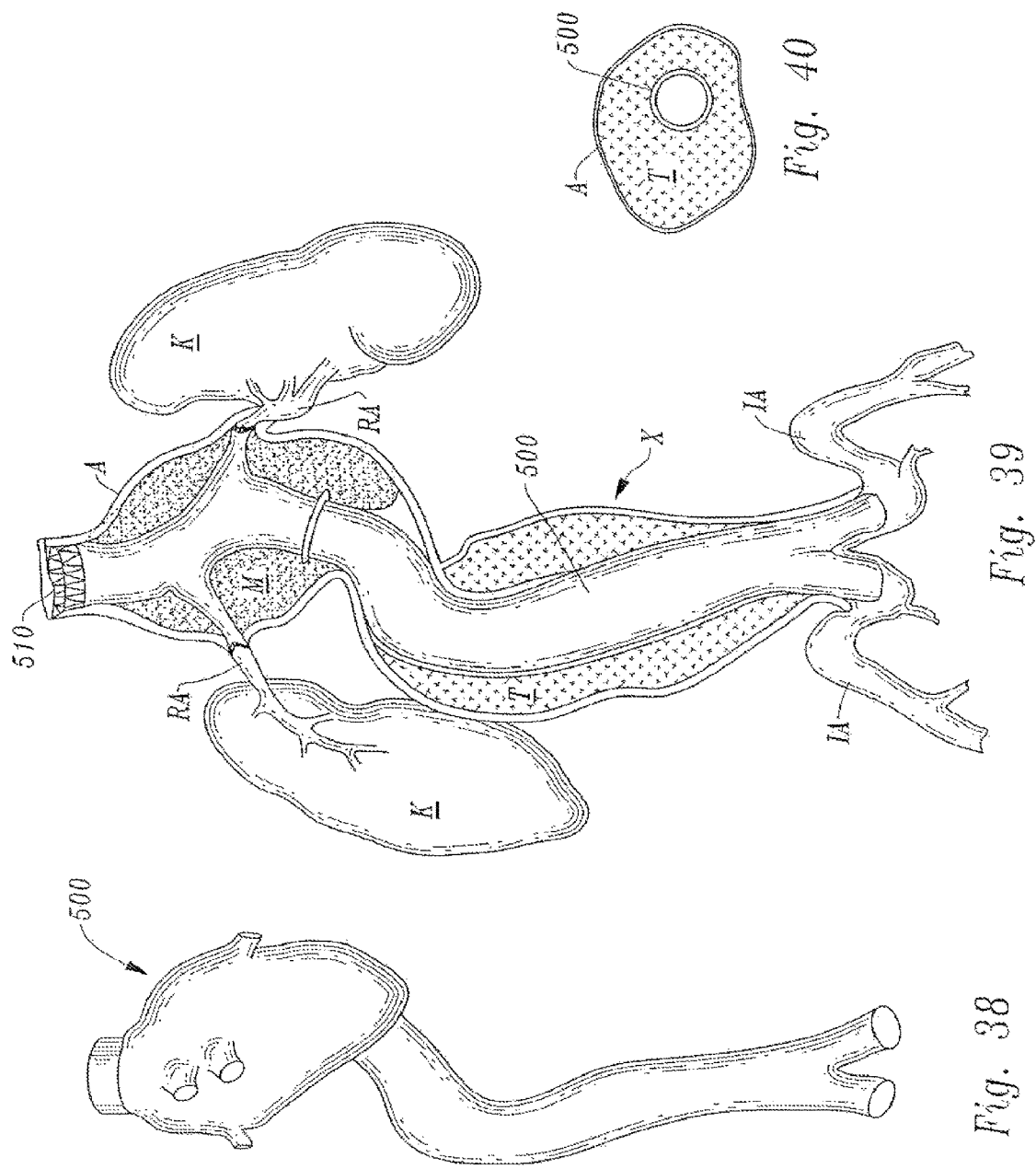

STENT-GRAFT WITH POSITIONING ANCHOR

The present application is a divisional of U.S. patent application Ser. No. 11/876,458, filed on Oct. 22, 2007, which is a divisional of U.S. patent application Ser. No. 10/668,901, filed Sep. 22, 2003, which claimed the benefit of provisional U.S. Application No. 60/412,501 filed on Sep. 20, 2002, the full disclosures of which are incorporated herein by reference.

BACKGROUND OF THE INVENTION

1. Field of the Invention

The following invention relates to stent-grafts for implantation into body lumens for support of the body lumens and to provide for repair and proper fluid flow through the body lumen. More particularly, this invention relates to stent-grafts which include anchors to keep the stent-grafts in a desired position, especially when implanted intraluminally, and most particularly to stent-grafts for intra-luminal implantation into the aortic artery of a human patient.

Stents are known in the surgical arts which are implanted intraluminally or otherwise and expanded to support the lumen and maintain fluid flow through the lumen. Such stents are often used in arteries where blood flow has become restricted with the stent propping the artery open to maintain proper fluid flow.

When an artery or other lumen becomes damaged, replacement of the damaged artery section with a graft may be indicated. Such grafts can be taken from other body lumens of the patient, or be in the form of an artificial prosthesis. Such grafts can replace a portion of the damaged artery or be implanted intraluminally or otherwise within the damaged section of the artery without removal of the damaged artery itself. The graft then supports blood flow within the damaged artery.

For grafts to function properly, they must be held in place where desired within the artery or other lumen. One technique for maintaining the proper position of the graft is to utilize a stent within a portion of the graft with the stent radially expanded to hold the portion of the graft adjacent the stent in position relative to the artery or other body lumen. Such a graft held in place by a stent can be provided as a single assembly for implantation, being then often referred to as a stent-graft. The stent can be coextensive with the graft or only provided at specific locations along the graft. The stent both acts to hold the graft in the desired position and also to maintain the desired open cross-section of the artery to maintain proper blood flow. When a graft is configured to both provide a substitute channel for flow of fluid through a body lumen and to keep the body lumen propped open, it can be referred to as a stent-graft also, even if it does not include a separate stent-like structure which is providing this support function.

One body lumen which is particularly suited to treatment of damage therein with a stent-graft is the aorta when it has developed an aneurysm. Such an aortic aneurysm can occur anywhere between the heart and the iliac arteries, resulting in an undesirable widening of at least a portion of the artery. Once such an aneurysm has formed, it is susceptible to rupture with a high probability of resulting mortality. It is known in the art to install a stent-graft in the aorta where the aneurysm exists. The stent-graft provides a new channel for blood flow through the region of the aneurysm, taking stress off of the arterial wall where the aneurysm exists so that the aneurysm will not rupture, and also channeling blood flow through the stent-graft so that even if the aneurysm were to rupture, internal bleeding would not result. The portion of the aorta which has the aneurysm therein can either be removed or remain in place if the stent-graft is delivered intraluminally or otherwise, within the portion of the aorta having the aneurysm.

One challenge presented by implantation of stent-grafts within the aorta is how to maintain the position of the stent-graft precisely where desired. It is desirable to avoid or minimize the need for suturing through the walls of the aorta so that the aorta walls can remain unpenetrated, and to avoid stressing the walls of the aneurysm by utilizing a stent which provides too great of radial pressure outward on the wall of the aorta. The relatively high blood flow and blood pressure existing within the aorta puts forces upon the stent-graft which present the possibility of dislodging the stent-graft from its desired position. Additionally, differing patient luminal geometries can cause a stent-graft which is well designed for an average patient to be either too large, too small or the wrong shape to be effectively held in place without damaging the aorta once implanted. Also, when the aneurysm is at a location on the aorta where a significant lateral artery is located, such as one of the renal arteries, one of the iliac arteries, or arteries extending off of the aortic arch, a typical prior art stent-graft will tend to block or limit flow to such lateral arteries, decreasing blood circulation to these portions of the patient, and decreasing the effectiveness of the procedure.

Accordingly, a need exists for implantable devices which can function effectively as a stent-graft and which can be placed within the aorta or other body lumens adjacent an aneurysm or other defect which will properly fit within the body lumen, avoid placing undesirable stress upon the body lumen, hold the stent-graft in the desired position and maintain blood flow to major lateral arteries off of the aorta, or other lateral lumens off of a primary lumen in which the device is implanted.

BRIEF SUMMARY OF THE INVENTION

This invention provides a stent-graft which is configured to be securely anchored within a body lumen such as the aorta. The stent-graft can be in the form of a positioning anchor alone, or a combination of a positioning anchor and a stent-graft extending from the positioning anchor, or in the form of a stent-graft alone with some of the anchoring aspects according to this invention built into the stent-graft itself. The positioning anchor according to this invention is preferably a double walled generally tubular structure with a void between an inner wall and an outer wall of the anchor. A primary fluid conduit is thus defined by the inner wall of the anchor, providing the generally tubular structure for the anchor. Lateral fluid conduits are also preferably provided which extend laterally from the primary fluid conduit and out of the anchor.

In a preferred embodiment of this invention, the contour of the walls of the anchor is provided in a custom fashion matching the particular luminal geometry of the patient in which implantation is to occur. Hence, the size, shape and position of the lateral fluid conduits within arms extending from the anchor are preferably precisely positioned where needed to allow these arms of the anchor to extend at least partially into the lateral arteries or other lateral lumens located within the patient at the site where implantation is to occur. Radially expandable stents can circumscribe the arms of the anchor to secure the arms within lateral lumens within the patient.

The void between the inner wall and outer wall of the anchor is preferably fellable with a fixation media so that the anchor can be inflated, brining the outer wall into contact with walls of the aorta or other body lumen at the implantation site. The fixation media can provide a rigidifying effect for the anchor, helping to maintain a geometry of the anchor within the aorta. Because the contour of the anchor matches the geometry of the patient at the implantation site, the anchor resists movement of the anchor, and any stent-graft coupled thereto, away from the implantation site.

Various different manufacturing methods are provided to form the walls of the anchor with the desired geometry, either with the anchor in a single walled form or in a double walled form. In the double walled form, the void can be totally open or can be spanned by interconnections functioning as "quilting" to maintain a maximum distance that the inner wall and outer wall can be spaced from each other. The anchor and other portions of the stent-graft can optionally be lined along the inner wall with a liner if such a liner is desired for the particular implantation procedure being conducted.

To provide the anchor and optionally a stent-graft coupled thereto with the desired geometry matching that of the aorta of the patient at the implantation site, the following procedure is preferably followed. Initially, patient luminal geometry is mapped utilizing imaging technology known in the art to create a data file corresponding with the patient's luminal geometry. This data file can then be used to create a three-dimensional virtual model of the patient geometry as well as a desired geometry for the anchor, any stent-graft, and optionally a lumen shaper balloon to be utilized to precisely expand and support the anchor during expansion and inflation/fixation of the anchor. These models are then sent in digital form to a rapid prototyping (RP) machine to create actual models of these structures, such as the anchor and the shaper balloon. These models can then either be used directly as a mandrel/mold for the forming of the anchor and/or shaper balloon or used indirectly to make such mandrels/molds. Once the mandrels and/or molds have been made for the various components needed for the implantation procedure, the anchor, shaper and other equipment are formed by applying appropriate material for the formation of these structures against the mandrel and/or mold. Finally, the mandrel and/or mold is removed to provide the finished custom shaped anchor, shaper balloon or other structure for use in the implantation procedure.

Deployment can occur in any desired fashion, with intraluminal implantation considered most preferred. With such intra-luminal implantation, the lumen shaper balloon is collapsed upon a catheter with the anchor collapsed down upon the lumen shaper balloon. The catheter is then inserted as is known in the art into the aorta or other body lumen in an intra-luminal fashion.

When the catheter is properly positioned, typically with the assistance of imaging technology to verify its position, the lumen shaper balloon is expanded to cause the anchor to be expanded with arms of the anchor extending into the lateral lumens for proper support of the anchor. The lumen shaper balloon then remains inflated while the fixation media is delivered into the void between the inner wall and outer wall of the anchor, causing inflation of the anchor. The lumen shaper balloon maintains the position of the inner wall during such filling of the void, causing the outer wall to expand away from the inner wall until it comes into contact with the luminal wall of the patient or other tissues or deposits which may have collected within the lumen and are to be abutted by the outer wall of the anchor. Once this fixation media has been delivered, and optionally has been allowed to set through a desired rigidity, the lumen shaper balloon can be deflated for removal of the lumen shaper balloon along with the catheter for completion of the procedure.

If a stent-graft is to be included along with the anchor, such a stent-graft can be implanted along with the anchor or in a secondary procedure with the stent-graft coupled to the anchor. The lumen shaper balloon can be configured to appropriately support the stent-graft and expand it into the desired position. If the stent-graft includes two walls with a void there between, fixation media can be utilized to fill this void in the stent-graft, either in a common procedure with the inflation of the anchor, or in a secondary procedure. Once any stent-graft has been properly positioned where desired and inflated with any fixation having taken place, any expansion shaper balloons on the catheter can be deflated and removed along with the catheter intraluminally out of the body lumen.

The implant including either the anchor alone, anchor and stent-graft or stent-graft alone remains in place with fluid flow through the lumen occurring through the interior tubular structure of the finally implanted structure, with the anchor or corresponding portions of the stent-graft fitting snugly within the patient's luminal geometry to maintain proper position for the anchor and/or stent-graft. Proper fluid flow is thus maintained through the primary fluid conduit of the lumen, as well as maintaining fluid flow through the lateral lumen extending from the primary lumen through lateral fluid conduits within the anchor and/or stent-graft.

Accordingly, a primary object of the present invention is to provide a stent-graft which securely maintains its position within a body lumen while avoiding or minimizing penetration of the luminal wall and avoiding or minimizing stress placed upon the luminal wall.

Another object of the present invention is to provide a stent-graft which can support fluid flow through a body lumen main pathway while also maintaining fluid flow to lateral lumens coupled to the primary lumen.

Another object of the present invention is to provide a stent-graft which can fill at least a portion of a space within an aneurysm within a body lumen and provide a channel for fluid flow past the location of the aneurysm.

Another object of the present invention is to provide a stent-graft which can be customized in shape and form to match particular luminal geometry of a particular patient.

Another object of the present invention is to provide a stent-graft which can be delivered intraluminally and remain securely affixed at an implantation site.

Another object of the present invention is to provide methods for manufacturing stent-grafts which include an inner wall and an outer wall with a void therebetween.

Other further objects of the present invention will become apparent from a careful reading of the included drawing figures, the claims and detailed description of the invention.

BRIEF DESCRIPTION OF THE DRAWINGS

FIG. 1 is a perspective view of an anchor for a stent-graft or for use alone, according to this invention.

FIG. 2 is a full sectional front elevation view of that which is shown in FIG. 1.

FIG. 3 is a perspective view of that which is shown in FIG. 1 after inflation of a void between an inner wall and an outer wall of the anchor.

FIG. 4 is a full sectional view of that which is shown in FIG. 3 and including associated patient geometry surrounding the anchor.

FIG. 5 is a perspective view of a combination anchor and stent-graft and with the anchor shown inflated.

FIG. 6 is a full sectional view of that which is shown in FIG. 5 shown within patient anatomy, and revealing the single walled structure of the stent-graft of this embodiment along with the double walled structure of the anchor of this embodiment.

FIG. 7 is a full sectional view of a cavity mold revealing one method for forming a single walled anchor and/or stent-graft according to this invention.

FIG. 8 is a full sectional view of a mandrel mold for use in the formation of a single walled anchor and/or stent-graft according to this invention.

FIG. 9 is a full sectional view of a rotating mold which can be used to form a single walled form of the anchor and/or stent-graft according to this invention.

FIG. 25 is a perspective view of the lumen shaper balloon according to the preferred embodiment for use in expanding the anchor of this invention.

FIG. 26 is a flow chart identifying the sequence of steps in the formation of a custom anchor, lumen shaper balloon and/or stent-graft with a particular geometry matching the particular luminal geometry of a patient to be treated with the device of this invention.

FIGS. 27-32 reveal steps in the process of delivering the anchor intraluminally to an implantation site.

FIG. 38 is a perspective view of a custom configured combined stent-graft with positioning anchor for treatment of a particular patient's aortic aneurysm with a double walled anchor and single walled stent-graft indicated.

FIG. 39 is a front elevation view of a patient's anatomy with the stent-graft with positioning anchor of FIG. 38 implanted therein and shown in full section.

FIG. 40 is a top plan full sectional view of a portion of that which is shown in FIG. 39 revealing the position of the single walled stent-graft surrounded by thrombus within the aorta of the patient.

DETAILED DESCRIPTION OF THE INVENTION

Figure 10:
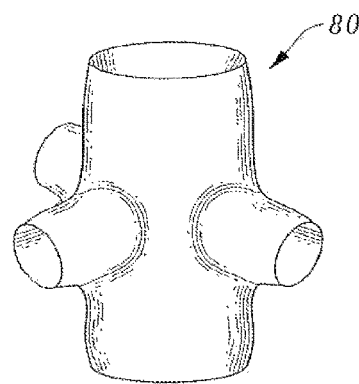
FIG. 10 is a perspective view of a sacrificial mandrel for use in the formation of the double walled anchor of FIG. 1.

Referring to the drawings, wherein like reference numerals represent like parts throughout the various drawing figures, reference numeral 10 is directed to an anchor (FIGS. 1-4) for use either alone or in combination with a stent-graft 40 to treat a damaged lumen such as an aorta A (FIG. 4) by providing a primary fluid conduit 22 for bypass fluid flow through the damaged area. The anchor 10 includes arms such as renal arms 16, 18 which extend laterally for positioning within the renal arteries RA or other lateral arteries LA to assist in maintaining a position of the anchor 10. The anchor 10 can be inflated, such as with a fixation media M to secure the position of the anchor 10 within the aorta A or other body lumen. A stent-graft 40 (FIG. 5) can be formed with or attached to the anchor 10 to further extend the primary fluid conduit for bypass fluid flow through the damaged portion of the aorta A.

In essence, and with particular reference to FIGS. 1-4, basic details of the anchor 10 of this invention are described. The anchor 10 is preferably double walled including an inner wall 20 inboard of an outer wall 30 (FIG. 2). A void 35 is provided between the walls 20, 30. Arms 16, 18 preferably extend laterally from a primary fluid conduit 22 extending through the anchor 10. When the void 35 is filled with fixation media M (FIG. 4) the outer wall 30 expands away from the inner wall 20 (along arrow B of FIG. 2) to fill a defect such as an aneurysm within the aorta A and to fix the position of the anchor 10.

The arms 16, 18 of the anchor 10 extend into lateral arteries such as the renal arteries RA to further assist in maintaining the desired position for the anchor 10. The anchor 10 can be utilized alone or can have a stent-graft 40 (FIGS. 5 and 6) attached thereto or formed therewith to extend the primary fluid conduit 22 as needed to bypass damaged portions of the aorta A. The stent-graft 40 can be single walled or double walled in form (FIGS. 41-44) to help fill and support any aneurismal space which is desired to be filled within the aorta A or other body lumen in which the implant is positioned.

More specifically, and with particular reference to FIGS. 1-4, particular details of the anchor 10 are described. The anchor 10 preferably has a geometry provided to match a geometry of the patient at the implantation site for the anchor 10. The anchor 10 can either be manufactured to approximate typical patient geometry or custom manufactured as described in detail below, to match a particular patient's luminal anatomy at an implantation site. For ease of illustration, FIGS. 1-4 depict an anchor 10 of somewhat simplified typical geometry for an anchor 10 configured for implantation at a junction between the aorta A of the patient and renal arteries RA leading to kidneys K of the patient.

The anchor 10 preferably has a particular geometry as follows. The anchor 10 is preferably generally tubular in form surrounding a primary fluid conduit 22 between an upper end 12 and a lower end 14. Multiple arms preferably surround lateral fluid conduits 24 extending away from the primary fluid conduit 22. Such arms can include a superior messenteric artery (SMA) arm 15 (FIG. 3) and first and second renal arms 16, 18. These arms 15, 16, 18 arc located where desired so that these arms 15, 16, 18 can extend at least partially into lateral arteries of the corresponding name within the patient.

The anchor 10 can be single walled to provide at least some of the desired function according to this invention, but is most preferably double walled in form. If the anchor 10 is single walled, it would typically be utilized in a patient which does not have an aneurysm or other defect at the location where the anchor 10 is to be implanted. The arms, such as the arms 15, 16, 18 of such a single walled anchor would be positioned into corresponding arterial pathways extending from the aorta or other lumen into which the anchor is to be implanted. Most preferably, radially expandable stents would be located adjacent these arms and radially expanded to bring such arms 15, 16, 18 of the anchor 10 into intimate contact with these lateral arteries. Additionally, a radial expandable stent can be utilized adjacent the upper end 12 and/or the lower end 14 to hold the ends 12, 14 of the anchor 10 securely in contact with the wall of the aorta A. If desired, additional attachment structures could be utilized including sutures, staples, or other attachment structures known in the art to secure such a single walled anchor at the desired implantation site. Such a single walled anchor according to this invention might support a single walled stent-graft, or a double walled stent-graft which would typically pass through a portion of the aorta A or other body lumen which is damaged. Such a single walled stent-graft would include a single wall which could merely extend the primary fluid channel away from the single walled anchor or could be provided as a separate piece configured to be attachable to such a single walled anchor, either outside of the patient or intraluminally during implantation of the single walled anchor and the stent-graft. The stent-graft 40 would typically have an upper end 42 (FIGS. 5 and 6) for formation with the anchor 10 or for attachment to the anchor 10.

According to the preferred embodiment, the anchor 10 is double walled, as particularly shown in FIGS. 1-4, or with varying geometries to match a particular geometry of a particular patient at a specific desired implantation site, either within the aorta or in other arteries or body lumens where implantation is desired. With such a double walled anchor 10, the anchor 10 is capable of undergoing an inflation and fixation procedure to assist in holding the anchor 10 in the desired implantation site location, and to fill an aneurysm or other defect space within the aorta A or other body lumen.

Specifically, after the anchor 10 has been positioned at the implantation site and oriented with the arms such as the arms 15, 16, 18, passing into corresponding lateral arteries, a fixation matrix M is delivered into the void 35 between the inner wall 20 and the outer wall 30. The inner wall 20 is preferably supported to prevent the inner wall 20 from collapsing inwardly into the primary fluid channel 22. Such support is preferably provided by a lumen shaper balloon which has been inflated inboard of the inner wall 20. One such lumen shaper balloon 110 is shown in FIG. 25 which could be utilized along with the anchor 10 of FIG. 1 during filling of the void 35 within the anchor 10.

Because the inner wall 20 is prevented from collapsing inwardly, the void 35 can only expand to receive the fixation matrix M by having the artery wall 30 expand away from the inner wall 20, along arrow B of FIG. 2. This expansion can both cause the outer wall 30 to expand into an aneurismal space or other defect and to enlarge the overall size of the anchor 10 to prevent the anchor 10 from moving away from its desired implantation site.

As particularly shown in FIG. 4, the anchor 10 has been expanded with the fixation matrix M so that the anchor 10 fills the space at the junction between the aorta A and the renal arteries RA such that the anchor 10 is securely held in position by the matching geometry between the anchor 10 and the patient geometry at that implantation site. Such a fixation methodology is generally analogous to the means by which a glove remains upon the hand due to matching geometry between inboard and outboard structures. This fixation methodology can be further enhanced by having the fixation media M formed of a material having a desired hardness which is either originally existing for the media M or which occurs in the media M after some transformation of the media M.

For instance, the media M could be initially presented into the void 35 in the form of a gas which undergoes a phase change or other transformation into a liquid or solid form either through a temperature change, a chemical reaction with agents located within the void 35 or a sufficient time for a gaseous matrix to set into a liquid or solid form. As another alternative, the fixation media M can be originally delivered as a liquid which could either remain liquid or undergo some level of firmness enhancement, such as by setting into a gel, or hardening into a solid, either by temperature change, chemical reaction or other setting procedure.

If necessary, or desirable, the media M could be delivered with multiple different components which would react together within the void 35 to solidify the media M within the void 35 to a desired level of firmness. Such firmness can both enhance the support with which the anchor 10 supports the wall of the aorta A, and can assist in holding the anchor 10 itself and any stent-graft 40 coupled to the anchor 10 fixed at the desired position within the patient.

The anchor 10 can be formed from a variety of different materials, either being formed from a single material or multiple different materials in combination. Most preferably, the material forming the anchor 10 is at least one layer of material which is impervious to fluid migration therethrough, either directly or by the inclusion of a fluid barrier liner, such as adjacent the inner wall 20 of the anchor 10. Most preferably, and to facilitate custom shaping of the contour of the anchor 10 to match the desired patient geometry at the implantation site, the anchor 10 is formed from a layer of moldable material. Such a moldable material could be in the form of a polymeric hydrocarbon. The anchor 10 itself, and/or an accompanying stent-graft 40 could be formed from parylene with a Dacron liner. The anchor 10 could be provided without a liner or formed entirely out of Dacron. Other materials exhibiting bio-compatibility and sufficient preclusion of fluid migration therethrough would also be suitable for formation of the anchor 10 and stent-graft 40 according to this invention.

The material forming the anchor 10 preferably is flexible to facilitate collapsing of the anchor 10 and the stent-graft onto a catheter for intra-luminal implantation. Such flexibility also assists in allowing the catheter to follow curving arterial pathways during intra-luminal delivery to the implantation site. Additionally, the material forming the anchor 10 and the stent-graft 40 is preferably substantially inelastic, at least within an operating range of pressures and forces with which the material encounters during implantation and function according to this invention. Some elasticity could be accommodated, provided that such an elasticity does not interfere with the function of the anchor 10 and stent-graft 40.

For particular discussion of the attributes of parylene and other materials from which the anchor 10 might be manufactured, particular reference is made to U.S. patent application Ser. No. 09/671,550, filed on Sep. 27, 2000, incorporated herein by reference.

The anchor 10 and other portions of the stent-graft 40 can be formed of any suitable method which provides the anchor 10 with the desired geometry and from the materials having the desired functional characteristics to function properly according to this invention. If the anchor 10 is to be formed in a single walled manner, one option includes use of a two-piece cavity mold 50 (FIG. 7), including an outer form 52 and an inner form 54. A cavity 56 between the forms 52, 54 is accessed through an entrance 58 for the material to enter the cavity mold 50. Such forming can generally be referred to as casting with the more specific manufacturing method utilizing such a mold including merely pouring the material into the mold, utilizing a vacuum to pull material into the mold, or utilizing some form of compression between the forms 52, 54 or compression or pressurization of the material at the entrance 58 to flow the material forming the anchor 10 entirely into the cavity mold 50.

With reference to FIG. 8, a mandrel mold 60 is provided which includes an inner mandrel 62 upon which a layer 64 of the material is deposited. Such material can be delivered, along arrow D of FIG. 8, to form the layer 64 upon the mandrel mold 60. Such delivery can occur by vapor deposition within a vacuum, dipping of the mandrel into fluid material for formation of the anchor 10 which can later harden, or with utilization of vacuum forming, such as where a layer of the material is sucked onto the inner mandrel 62 by small vacuum holes formed within the inner mandrel 62.

With particular reference to FIG. 9, a rotating mold 70 is shown which includes an outer form 72 only, with an entrance 74 leading into a void within the outer form 72. A layer 76 is formed upon surfaces within the form 72. This layer 76 can be formed such as by filling the mold 70 with material through the entrance 74 and then spinning the mold 70 until a layer of the material with which the anchor is to be formed is applied to surfaces of the form 72 by forces applied along arrow E. Alternatively, vapor deposition can occur within the mold 70, gas pressure can be applied to blow the material against surfaces of the mold 70, or a vacuum forming technique can be utilized where small vacuum ports are included within the outer form 72 extending into the cavity within the mold 70 to suck the material forming the layer 76, typically originally provided in a solid sheet form, up against surfaces of the mold 70. Such techniques shown in FIGS. 7-9 are suitable for forming a single walled anchor, most particularly. With some modification, some of these manufacturing methods could similarly be utilized for forming at least one of the walls of a double walled anchor 10 or for formation of both the inner wall 20 and the outer wall 30 of such an anchor 10.

Figure 11:
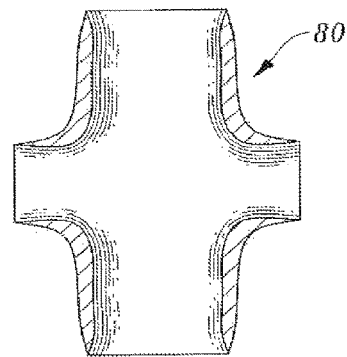
FIG. 11 is a full sectional view of the sacrificial mandrel of FIG. 10.
Figure 12:
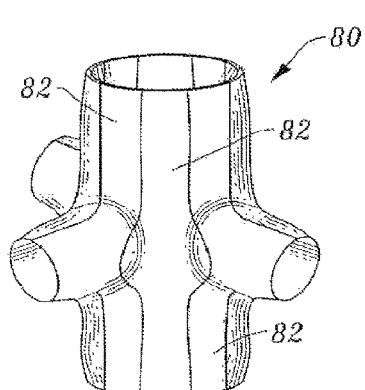
FIG. 12 is a perspective view of the sacrificial mandrel revealing cut lines for the cutting of the mandrel into sections, as a first step in a quilting process to provide interconnections between an inner wall and an outer wall of an anchor formed with the sacrificial mandrel shown therein.

With particular reference to FIGS. 10 and 11, details of a sacrificial mandrel 80 are shown which can be utilized according to a preferred embodiment to form the double walled anchor 10 of this invention. The sacrificial mandrel 80 is essentially identical in size and contour to the void 35 of the anchor 10, such as that shown in FIGS. 1 and 2. Such a sacrificial mandrel 80 can be manufactured utilizing various suitable casting or other forming techniques.

Preferably, the sacrificial mandrel 80 would be formed of a material which can be readily destroyed for removal after formation of the double walled anchor 10 about the sacrificial mandrel 80, leaving the void 35 within the anchor 10. For instance, the sacrificial mandrel 80 can be formed of a water soluble material, so that once it comes into contact with water it liquefies and can be removed leaving the void 35 within the anchor 10.

As another alternative, the sacrificial mandrel 80 can be formed from a material which easily dissolves when an appropriate solvent is applied. For instance, the sacrificial mandrel 80 could be formed of a foam material, such as Styrofoam, which would react with a solvent such as acetone to pass entirely into solution and be poured out of the void 35 in the form of a liquid. Such removal of the sacrificial mandrel 80 would typically occur by forming a hole somewhere in the anchor 10 leading into the void 35, or removal of the sacrificial mandrel 80 after it has been so dissolved. Other alternatives include forming the sacrificial mandrel 80 from a material which can be readily oxidized, such as by combustion or otherwise gasified by a chemical reaction to allow the sacrificial mandrel 80 to be removed in the form of a gas out of the void 35 within the anchor 10.

As another alternative, the sacrificial mandrel 80 could be formed from a solid material, such as a wax, which has a suitable melting point so that it can merely be heated until it changes phase into a liquid or gaseous form, to then be removed from the void 35 within the anchor 10.

Similarly, the sacrificial mandrel 80 could be formed from an easily fracturable solid material, such that sharp blows to the anchor 10 with the sacrificial mandrel 80 included therein would cause the sacrificial mandrel 80 to shatter into small solid pieces which could be removed from an appropriate hole leading into the void 35 within the anchor 10. Such shattering could also be provided by appropriately tuned vibrations, or ultrasonic waves, which might be directed at the sacrificial mandrel through the walls 20, 30 of the anchor 10.

While it is preferable that the sacrificial mandrel 80 be removed from the void 35, it is also conceivable that the sacrificial mandrel 80 would remain in some form within the void 35 and be implanted along with the anchor 10. For instance, if the sacrificial mandrel is formed of a collapsible foam material which has any resiliency and shape memory, it could be collapsed upon a catheter with an appropriate sheath to hold the anchor lain its collapsed form. Once reaching the implantation site, the retraction of the sheath would cause such resilient foam to expand within the void 35 to the desired expanded position. If additional expansion is required, additional material could be provided along with the material forming the sacrificial mandrel 80, to further increases the size of the void 35 and/or to solidify the material forming the sacrificial mandrel 80 further, to enhance a firmness of the anchor 10. In such an embodiment, the sacrificial mandrel 80 would not necessarily be sacrificed, but rather remain in a position within the void 35 of the anchor 10.

Figure 13:
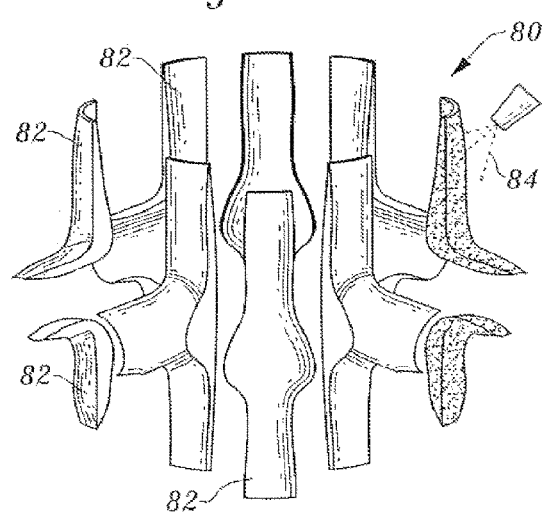
FIG. 13 is a perspective view of that which is shown in FIG. 12 after cutting of the mandrel into sections and at the beginning of a coating process for individual sections of the sacrificial mandrel.
Figure 14:
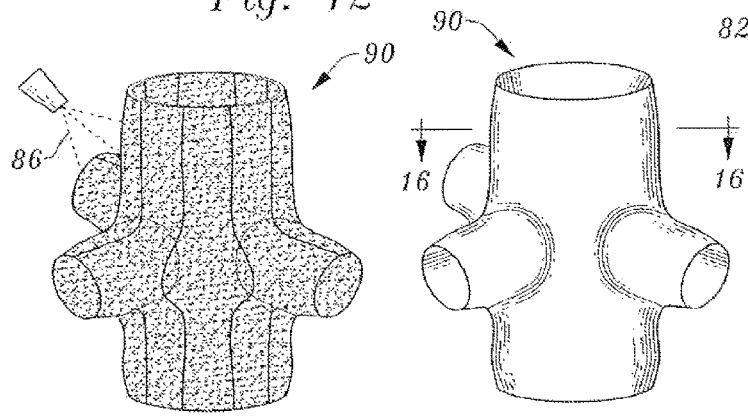
FIG. 14 is a perspective view of the sacrificial mandrel after having been reassembled and receiving a second coating to form the anchor with quilting included therein.
Figure 15:
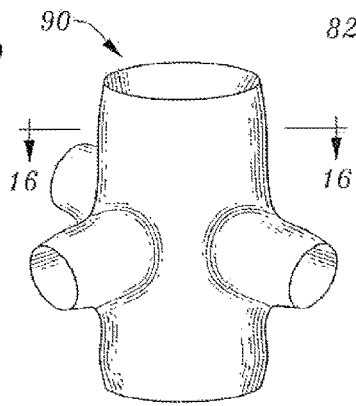
FIG. 15 is a perspective view of the anchor with internal quilting not visible within an interior thereof.
Figure 16:
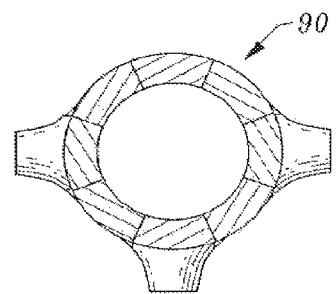
FIG. 16 is a full sectional top plan view of the anchor and mandrel together and revealing the orientation of the quilting interconnection between the inner wall and the outer wall and with the sacrificial mandrel still included therein.

With particular reference to FIGS. 12-16, details of a first quilting method are described which allows for the providing of interconnections between the inner wall 20 and outer wall 30 of the anchor 10 or corresponding portions of a double walled stent-graft, such as the toroidal sections of the stent-graft shown in FIGS. 35 and 41-44. When such interconnections are desired, the sacrificial mandrel 80 can be sliced along lines dividing the sacrificial mandrel 80 into separate sections 82 (FIG. 13). Such sections would be cut in orientations where the interconnection walls would be desired. Individual sections 82 would then be coated with a first coating 84 (FIG. 13) so that each section 82 of the sacrificial mandrel 80 is entirely coated with the material with which the anchor 10 is to be formed. Next, the sections 82 would be reassembled (FIG. 14) to again form the sacrificial mandrel 80 as it was originally constructed. A second coating 86 is then applied to the exterior of the outer wall 30 and the interior of the inner wall 20. This second coating 86 reattaches separate sections 82 of the sacrificial mandrel 80 back together. When the pieces of the original sacrificial mandrel 80 are later removed, multiple separate chambers are included within the void 35.

Figure 18:
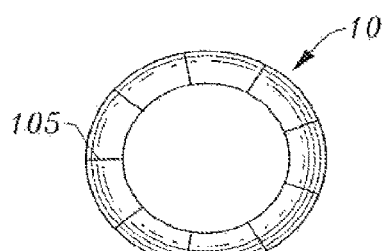
FIG. 18 is a full sectional top plan view of a portion of that which is shown in FIG. 15 or 17 after removal of the sacrificial mandrel from within the voids of the anchor and revealing one orientation for the quilting between the inner wall and the outer wall of the anchor.
Figure 19:
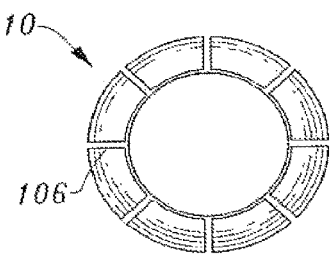
FIG. 19 is a top plan view similar to that which is shown in FIG. 18, but illustrating thicker interconnections between the inner wall and the outer wall of the anchor.

As described above, such interconnections can assist in resisting collapse of the inner wall 20 and constriction of the primary fluid conduit 22 during inflation of the void 35 with fixation media M. The finished anchor/mandrel combination 90 has a similar form (FIG. 15) as the sacrificial mandrel 80 (FIG. 10) and the desired finished construction for the anchor 10 (FIG. 1). However, the multiple interconnections extend between the inner wall 20 and outer wall 30, as particularly shown in the sectional view of FIG. 16. Hence, after the sacrificial mandrel 80 material has been removed, the sectional configuration of the anchor 10 can be as shown in FIG. 18. Alternatively, if the first coating 84 (FIG. 13) is thicker, than thicker interconnections provide wide quilting 106 between chambers in the void 35 (FIG. 19).

Figure 17:
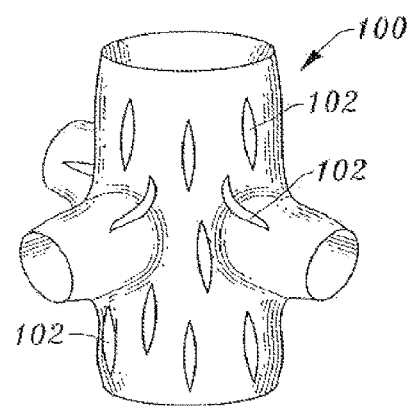
FIG. 17 is a perspective view of a quilting mandrel which includes slits therein to form quilting interconnections between the inner wall and the outer wall of the anchor after the quilting mandrel is coating with the material forming the anchor.
Figure 20:
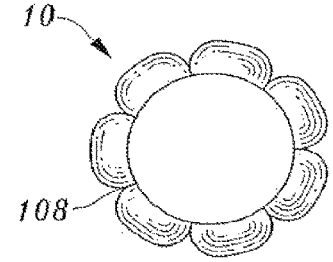
FIG. 20 is a sectional top plan view similar to that which is shown in FIGS. 18 and 19, but with interconnections with irregular widths forming quilting between the inner wall and the outer wall of the anchor.

In accordance with a second quilting method, FIG. 17 provides a quilting mandrel 100 similar to the sacrificial mandrel 80 (FIG. 10) except that slits 102 are provided at various locations passing through the quilted mandrel 100. These slits 102 can have various different widths or tapering widths depending on whether thin quilting 105 (FIG. 18) is desired or wide quilting 106 (FIG. 19) is desired or whether tapered quilting 108 (FIG. 20) is desired.

When the quilting mandrel 100 is sprayed or vapor deposited with the material forming the anchor 10, some of the material passes through the slits 102 to form the quilting between the inner wall 20 and the outer wall 30 of the anchor 10. When the sacrificial quilting mandrel 100 is removed, the void 35 is provided with interconnection regions existing where the slits are provided within the quilting mandrel 100.

Figure 21:
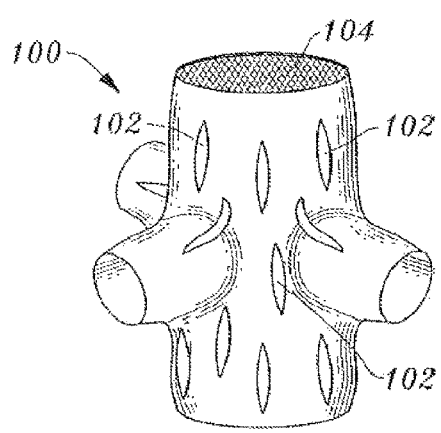
FIG. 21 is a perspective view of the quilting mandrel with a liner included therein.
Figure 22:
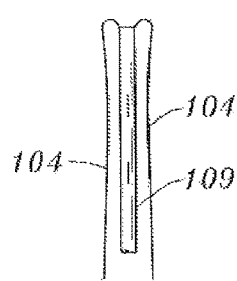
FIGS. 22-24 reveal a sequence of steps associated with the positioning of the liner within the mandrel or onto an anchor after formation of the anchor upon the mandrel, especially when a double wall of the liner material is desired to be provided adjacent the inner wall of the anchor.
Figure 23:
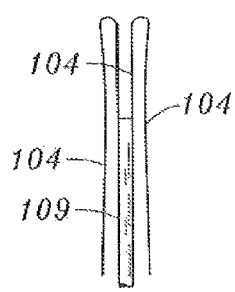
Figure 24:
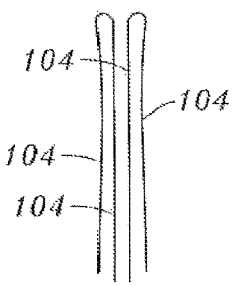

If desired, the anchor 10 can include a liner 104, such as adjacent the inner wall 20. Such a liner 104 is shown in FIG. 21 within the quilting mandrel 100. This liner 104 could be provided along with the quilting mandrel 100 so that formation of the walls 20, 30 occurs with the liner 104 in position to bond the liner 104 to the material forming the walls 20, 30. Alternatively, the liner 104 can be provided later after forming the inner wall 20 and outer wall 30 of the anchor 10 upon the sacrificial mandrel 80 or the quilting mandrel 100. Such a liner 104 can be attached to the anchor 10 before implantation of the anchor 10 or such a liner 104 can be provided during implantation or after implantation of the anchor 10.

Where a double walled liner 104 is desired, a rod 109 can be utilized to double back the liner 104 upon itself. Such a rod 109 can be one portion of a circular tube such that a double walled liner 104 becomes a quadruple walled liner 104, when the rod 109 is moved downwardly such as in FIGS. 22-24, or can be changed from a single walled liner 104 to a double walled liner 104 if the rod 109 is in the form of a single rod 109 between two liners 104.

The liner 104 can include holes therein adjacent where lateral arms are located within the anchor 10, or can be continuous in those locations in a fashion precluding blood flow to lateral arteries, if desired. For instance, if a lateral artery is not particularly needed for blood flow, such a lateral artery can merely be utilized as an anchoring point for the arms of the anchor 10, and not maintain blood flow therethrough. Preferably however, any liner 104 includes appropriate holes adjacent the arms of the anchor 10 so that blood flow is maintained through the lateral arteries adjacent where the anchor 10 is implanted.

With particular reference to FIG. 25, details of the shaper balloon 110 are described. As discussed above, the shaper balloon 110 is provided to expand the anchor 10 after translation of the anchor 10 with the catheter to the implantation site. The lumen shaper balloon 110 is also provided to support the inner wall 20 of the anchor 10 during inflation of the void 35 in the anchor 10 with fixation media M. The lumen shaper balloon 110 preferably includes a geometry matching generally that of the inner wall 20 of the anchor 10. The lumen shaper balloon 110 thus includes a top 112 spaced from a bottom 114. Arms 116 extend away from the exterior surface of the shaper balloon 110.

The shaper balloon 110 is preferably enclosed so that the top 112 and bottom 114 are enclosed with at least one access port for the delivery of an inflation fluid into the lumen shaper balloon 110. Preferably, knobs 118 are located at the ends of each of the arms 115 which are enclosed to allow the lumen shaper balloon 110 to be inflated without any holes where leakage would occur. These knobs 118 preferably inflate to a larger diameter than adjacent arms. The knobs 118 can be located adjacent where radially expandable stents are to be expanded between the anchor 10 and the lateral artery walls of the patient. The knobs 118 thus provide the radial force necessary to expand the radial expandable stent to the diameter desired. As an alternative, such radial expandable stents can be delivered in a separate procedure after general positioning of the anchor 10.

Preferably, the shaper balloon 110 is custom manufactured to a geometry matching a contour of the particular patient's body lumen geometry where the anchor 10 is to be implanted. Hence, a custom shaper balloon 110 is provided particularly adapted for expansion, inflation and proper positioning of the custom anchor 10 at the implantation site. The lumen shaper balloon 110 would typically be a single walled structure, such that the manufacturing techniques particularly illustrated in FIGS. 7-9 and discussed in detail above would be suitable for formation of the lumen shaper balloon 110.

With particular reference to FIG. 26, details of the process to be followed in custom manufacture of the anchor 10, the lumen shaper balloon 110 and any custom manufactured stent-grafts 40 are described. Initially, patient imaging information in the form of X-rays, computer tomography (CT) scans, ultrasound data, magnetic resonance imaging (MRI) data or other imaging data are acquired and converted into a data file such as that which can be read by a computer aided drafting (CAD) file or other corresponding data coding methodology. This imaging information can be viewed, such as by a physician or other medical treatment planners to determine how best to treat any defects in the body lumens being imaged.

On computer displays viewing the data, the treatment planner can construct a desired geometry for the anchor 10 and/or stent-graft 40 which would match the particular patient's luminal geometry at the treatment site. Some or all of this process of constructing a desired geometry for the anchor 10 and/or the stent-graft 40 could similarly occur in an automated fashion by a computer recognizing the geometry of the patient's body lumen and taking appropriate measurements to construct a desirable anchor 10 and/or stent-graft 40.

Once such virtual models of the anchor 10 have been created, an automated or manual process can be utilized to define desired geometry for the lumen shaper balloon 110 to be utilized in positioning and expanding the anchor 10. These virtual models also digitally describe the geometry of mandrels and/or molds to be used in forming the actual devices which will be used in the implantation procedure.

Data files corresponding with the geometry of the desired anchor 10 and desired lumen shaper balloon 110 are then sent to a rapid prototyping (RP) machine, such as that provided by Z-Corp or 3-D Systems. The rapid prototyping machine then creates actual three-dimensional models, preferably of full size, for the anchor 10 and the lumen shaper balloon 110. These 3-D models of the anchor 10 and lumen shaper balloon 110 can then either be used directly or indirectly to form mandrels or other molds which will then be used in formation of the final anchor 10 and lumen shaper balloon 110.

Finally, in the case of a sacrificial mandrel 80, the mandrel is removed as is discussed in detail above to provide voids 35 where desired within the anchor 10. The final shaper balloon 110 and anchor 10 can then be collapsed upon a catheter or other deployment device for use in the implantation procedure, to be delivered to the implantation site.

With particular reference to FIGS. 27-32, the preferred method for intra-luminal implantation of an anchor 150, similar to that of the anchor 10, is described. In these figures, a lateral view is provided with the primary fluid conduit extending vertically in the form of a human patient's aorta and with lateral arteries in the form of the superior messenteric artery (SMA) and a second lateral artery LA, such as the inferior messenteric artery. Renal arteries are not shown in this sectional view, but would typically also be included in the geometry of the anchor 150 and shaper balloon 160.

Initially, a delivery catheter 120 is provided which includes the shaper balloon 160 collapsed upon the delivery catheter 120 and with the anchor 150 overlying and collapsed upon the shaper balloon 160. A sheath 140 overlies the anchor 150 and shaper balloon 160 to assist in holding the shaper balloon 160 and anchor 150 in their collapsed configuration.

The delivery catheter 120 can then be fed through an insertion site, such as in the femoral artery of one of the legs of the patient, up to the aorta A or other implantation site. A guide wire 122 is preferably provided to assist in steering the delivery catheter 120 along the desired arterial pathway up to the aorta A. Once the delivery catheter 120 has reached the implantation site where an aneurysm X exists, and adjacent the lateral arteries to which the anchor 10 has been custom manufactured, the delivery catheter 120 is then rotated to the desired orientation. Radiopaque markers can be included upon the delivery catheter 120, the sheath 140 or upon the anchor 150 or shaper balloon 160 to determine both the position of the delivery catheter 120 and the orientation of the delivery catheter 120.

The sheath 140 is then retracted to expose the anchor 150. Preferably, a seal balloon 130 is provided near a tip of the delivery catheter 120. This seal balloon 130 can be initially inflated, such as through a fluid delivery conduit within the delivery catheter 120 and with an outlet at the seal balloon 130. The seal balloon 130 can thus be expanded to block off the aorta A. Preferably, a tip of the delivery catheter 120 includes a bypass inlet 124 to a hollow center of the delivery catheter 120, or other pathway extending to the bypass outlet 126. In this way, blood flow F can be diverted through the delivery catheter 120 during the positioning, expansion and inflation procedure for the anchor 150.

Figures 27, 28, 29:
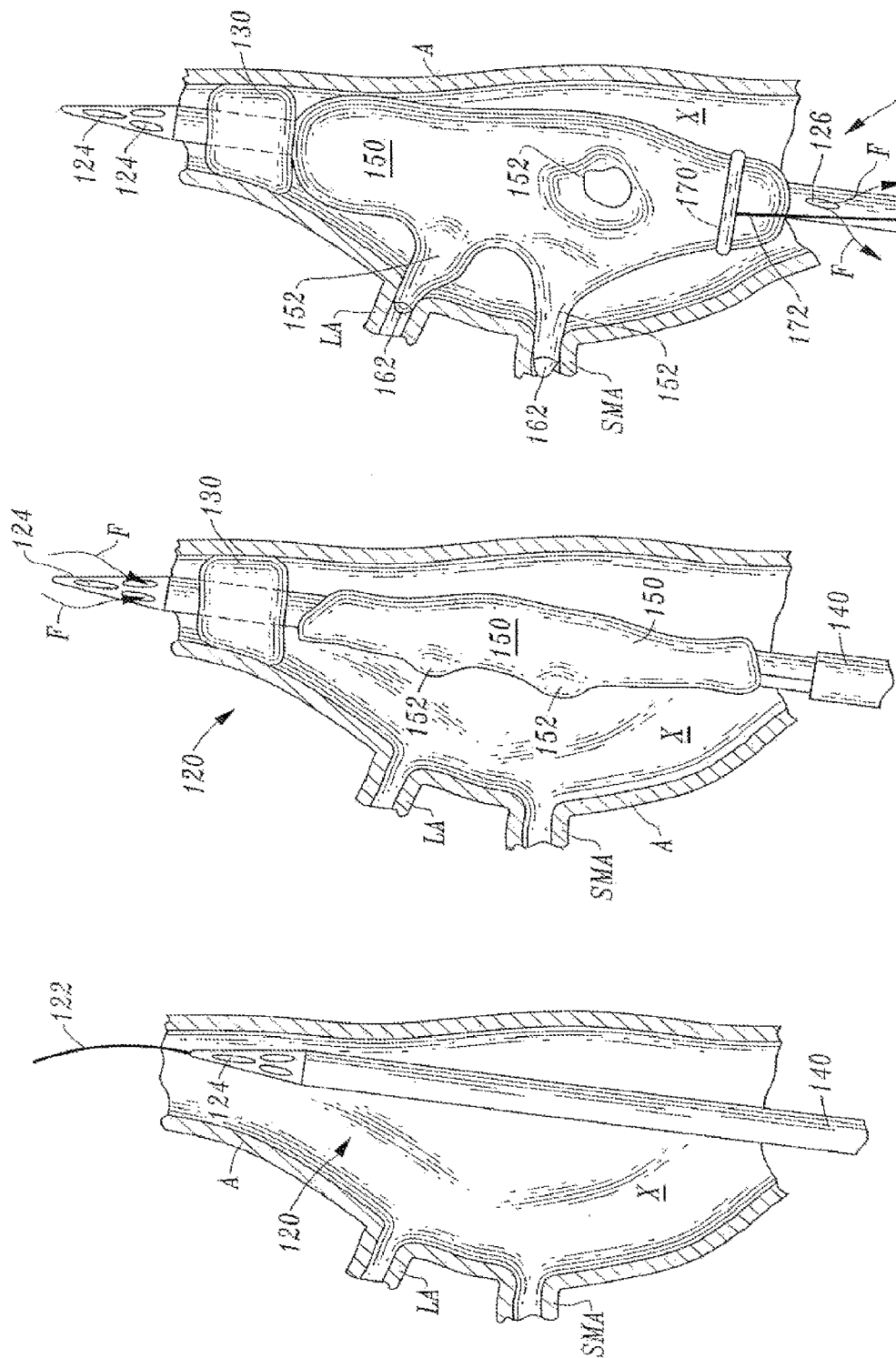

The shaper balloon 160 is then inflated by delivery of an appropriate inflation fluid into the shaper balloon 160. This causes the anchor 150 to be expanded to its fully expanded (but uninflated) form (FIG. 29). As inflation of the shaper balloon 160 occurs, arms 152 in the anchor 150 begin to protrude with the assistance of the arms 162 of the shaper balloon 160. The delivery catheter 120 can be further rotated if necessary to make sure that the arms 152 are oriented where desired so that the arms 152 feed into the lateral artery LA and superior messenteric artery SMA for proper positioning of the anchor 150. When the shaper balloon 160 has been fully inflated, the entire aneurysm X has not typically been entirely filled. However, the arms 152, of the anchor 150 should extend into the lateral arteries LA extending off of the aorta A.

If desired, a collar 170 can be provided within the anchor 150 which is in the form of a separate void which can be initially filled to provide added structure to the anchor 150 and to further assist in preventing the anchor 150 from slipping within the aorta A. Such filling of the collar 170 can occur through a filler tube 172 leading to the collar 170. Once the expanded but uninflated anchor 150 is properly positioned with its arms 152 extending into the lateral arteries extending through the aorta A, the anchor 150 is ready for inflation.

Fixation media M is then delivered through the media delivery tube 180 (FIG. 31) to expand the outer wall 156 away from the inner wall 154 and fill the void 155 between these walls 154, 156. As discussed in detail above, the fixation media M is then allowed to harden to the desired firmness according to the type of fixation media M utilized. If desired, radial expandable stents can be radial expanded within the arms 152 of the anchor 150 to secure the arms 152 where desired within lateral arteries, and/or adjacent an upper end and/or a lower end of the anchor 150.

Finally, the lumen shaper balloon, which has remained inflated to ensure that the primary fluid conduit through the anchor 150 remains fully open during setting and filling of the void 155 with the media M, can be deflated along with the seal balloon 130. The delivery catheter 120, fill balloon 130 and lumen shaper balloon 160 can then be retracted out of the anchor 150.

If portions of a stent-graft are coupled to the anchor 150, they can be inflated before movement of the delivery catheter 120, or with a balloon such as the seal balloon 130 utilized to expand the stent-graft as the delivery catheter 120 is retracted. Once the delivery catheter 120 and lumen shaper balloon 160 has been removed, blood flow F' occurs through the anchor 150 and with blood allowed to flow through the lateral arteries coupled to the aorta A at the implantation site.

While this implantation procedure has been particularly described with regard to the anchor 150 being inflated at a junction of the aorta A and renal arteries RA, a similar procedure could be utilized for delivery of an anchor to the aortic arch, or to a location above the renal arteries, or to a location below the renal arteries, depending on the particular treatment plan indicated for the patient's condition. An analogous delivery procedure would be utilized for the expansion and inflation of a double walled stent-graft according to this invention with the exception that no arms would be included which would require positioning into lateral arteries. Such a stent-graft can be provided along with the anchor or implanted in a separate follow-up procedure after positioning of the anchor.

Figure 33:
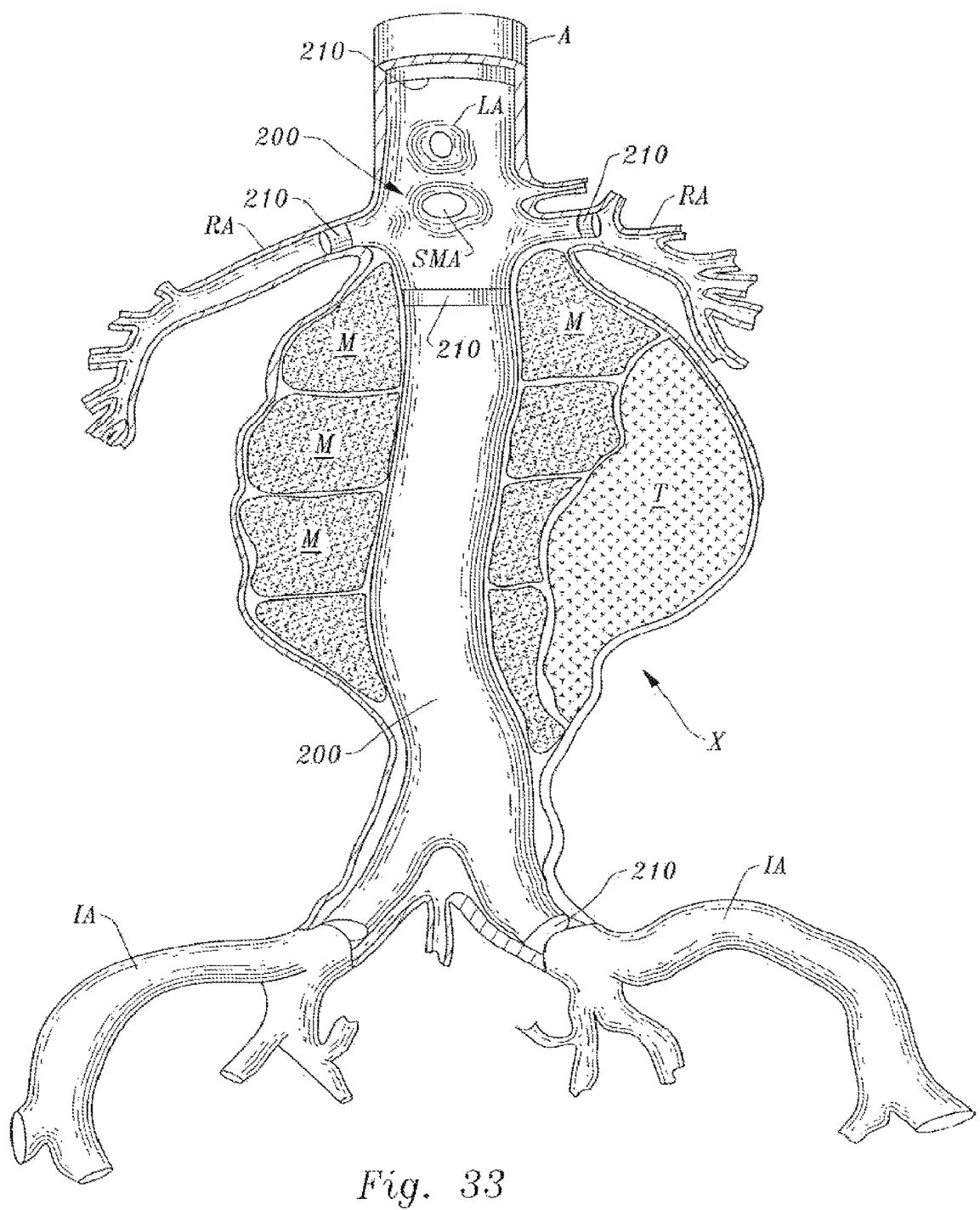
FIG. 33 is a front elevation view in partial section of a human patient's aorta with a customized stent-graft with anchor according to this invention implanted therein.

With particular reference to FIGS. 33-44, various particular examples are provided of different luminal defects, and particularly aortic aneurysms, with varying implants in the form of anchors and stent-grafts provided to treat such typical hypothetical cases. With particular reference to FIG. 33, an aneurysm X is presented within an aorta A which is primarily below the renal arteries RA and above the iliac arteries IA, but close to the iliac arteries IA. This aneurysm X includes a significant amount of thrombus T in at least one portion of the aneurysm X. A stent-graft with renal anchor 200 is custom manufactured to have a geometry similar to that depicted in FIG. 33.

Specifically, the anchor portion is generally in the form of a single walled anchor which includes stents 210 in arms of the anchor which extend into the renal arteries, the superior messenteric artery SMA and other lateral arteries LA. Additional stents 210 support upper and lower ends of the anchor adjacent walls of the aorta A.

A series of toroids are manufactured along with the stent-graft portion of the implant 200. These toroids are generally similar to those shown in the stent-graft with positioning anchor 600 of FIGS. 41-44. Once these toroidal sections have been filled with fixation media M, they fill portions of the aneurysm X which are not already filled with thrombus T. A final channel is provided which extends through the aneurysm X down to the iliac arteries IA. In this case, the stent-graft portion splits into two separate channels to feed each of the iliac arteries IA separately. Stents can be provided at the ends of these separate channels to support the lower most ends of the implant 200.

Figure 34:
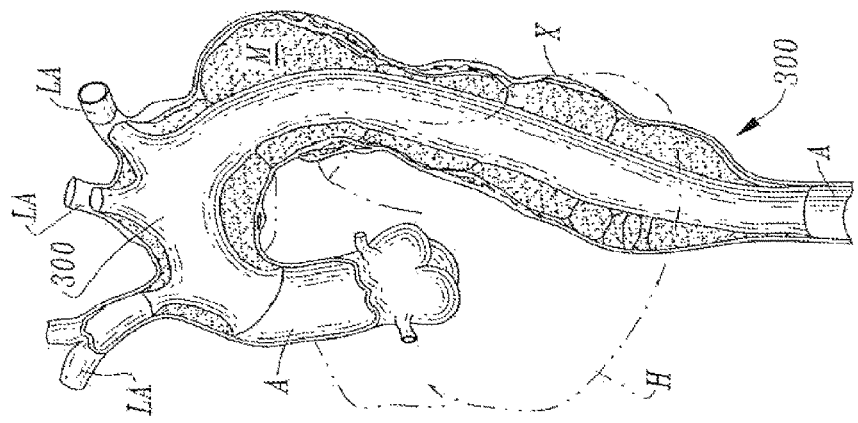
FIG. 34 is a front elevation view in partial section of a patient's aorta with an anchor and stent-graft implanted therein especially at an aortic arch to treat an aneurysm therein.
Figure 41:
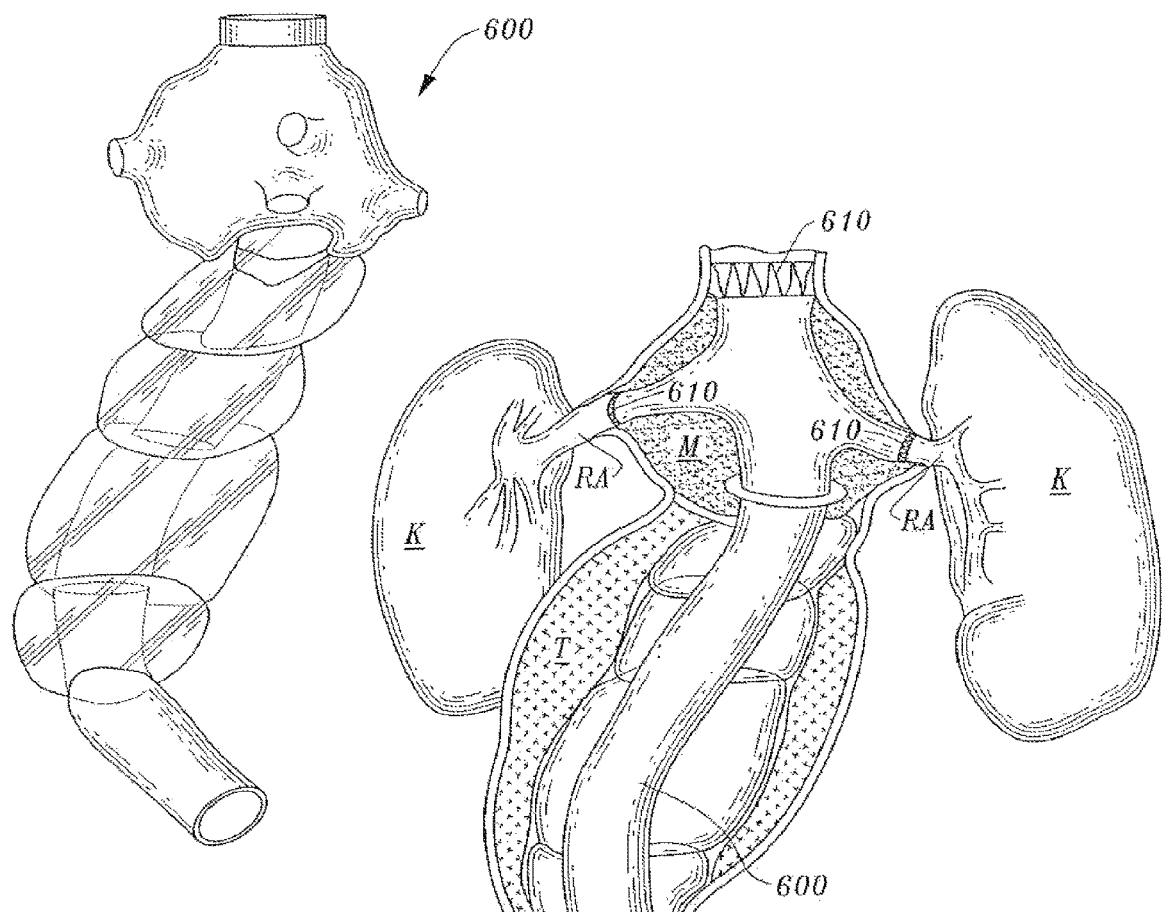
FIG. 41 is a perspective view of an alternative combination stent-graft with positioning anchor where both the positioning anchor and the stent-graft are formed together and are double walled in construction, having been custom manufactured to match a particular patient's arterial geometry.

With particular reference to FIG. 34, a stent-graft with aortic arch anchor 300 is depicted. In this example, the patient's aortic arch and portions of the aorta above the renal arteries includes an aneurysm therein. The position of the patient's heart H is shown in broken lines for reference. The aneurysm X both exists within the aortic arch and below the aortic arch. An anchor is provided which includes two walls so that the anchor portion of the implant can be expanded, as well as toroidal sections on the stent-graft portion of the implant 300. The aortic arch anchor is custom manufactured to have lateral artery arms positioned where desired to match the particular patient geometry, so that the aortic arch anchor, once expanded, will securely hold both the anchor and the stent-graft in the desired position. Media M fills both the void within the aortic arch anchor and in the stent-graft, extending from the aortic arch anchor to fill excess space within the aneurysm X.

Figure 36:
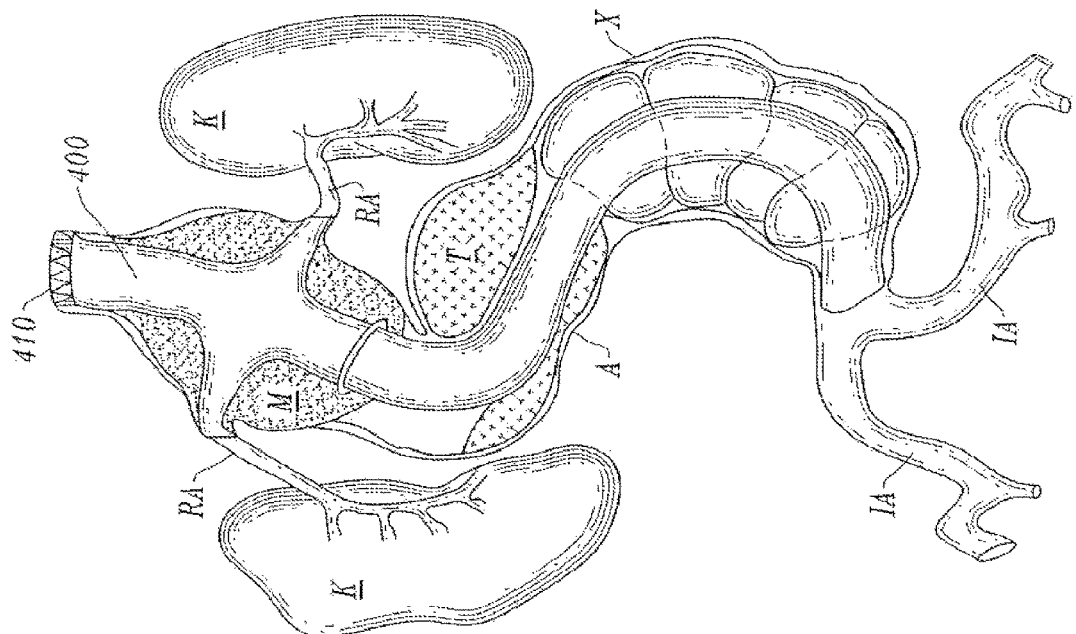
FIG. 36 is a front elevation view of a patient with the stent-graft and anchor of FIG. 35 implanted within the patient and shown in full section.
Figure 35:
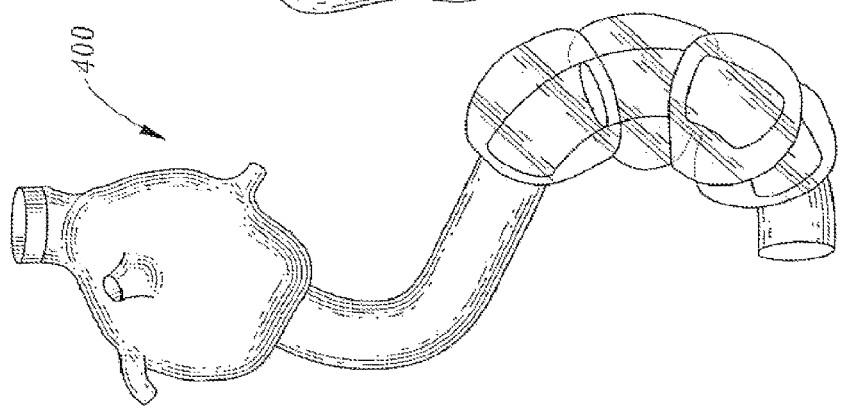
FIG. 35 is a perspective view of a stent-graft with positioning anchor and with a portion of the stent-graft shown with a single walled and with a portion of the stent graft including separate toroidal sections in the form of double walls for at least a portion of the stent-graft.
Figure 37:
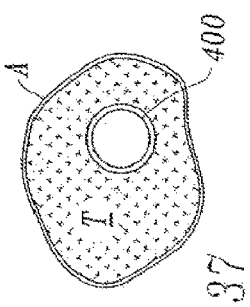
FIG. 37 is a full sectional view of a portion of that which is shown in FIG. 36 adjacent where a single walled portion of the stent-graft is provided and where thrombus is present within an aortic aneurysm within the patient.

With particular reference to FIGS. 35-37, a third example is provided. In this example, the patient has an aortic aneurysm which includes both a junction between the aorta and the renal arteries and an aneurysm X extending down to near the iliac arteries IA. However, a sufficient amount of thrombus T exists in a midpoint of the aneurysm that the stent-graft portion of the proposed implant 400 need only be a single walled stent-graft at upper portions thereof. Stent 410 supports upper end of implant 400 adjacent walls of the aorta A. Lower portions of the stent-graft include toroidal fillable sections so that the stent-graft is double walled in this lower region.

Also, the anchor portion of the implant 400 is double walled, similar to the embodiment of FIGS. 3 and 4. This example illustrates how portions of the aneurysm X can be filled with media within the anchor and portions of the aneurysm X can be filled with media through the toroids on the stent-graft, with still further portions of the aneurysm X filled with the thrombus T already existing within the aneurysm X, and with potentially other portions of the aneurysm X remaining unfilled where it is deemed that such a void is not disadvantageous. In this embodiment the aneurysm stops sufficiently short of the iliac arteries IA. Hence, a single tubular ending to the stent-graft is custom provided for termination of the lower end of the implant 400. FIG. 37 provides a cross-section of a portion of the stent-graft which is single walled, and illustrating how the thrombus T can act to support the stent-graft within the aorta A.

FIGS. 38-40 provide a fourth example for the function of the invention of this application. In this example, the patient has an aneurysm with a significant amount of thrombus T in the lower portion thereof, but without a significant amount of thrombus near the junction with the renal arteries RA. In this example, a stent-graft with positioning anchor 500 is manufactured as shown in FIG. 38. This stent-graft with positioning anchor is configured to utilize the renal arteries primarily for anchoring of the anchor and the stent-graft portions of the implant 500. Stent 510 supports upper end of anchor 500 adjacent walls of the aorta A.

Fixation media M is utilized to expand the anchor portion of the implant 500 to fill the void adjacent the renal arteries RA. Because lower portions of the aneurysm X include a significant amount of thrombus T which is already effectively positioned to support the stent-graft portion of the implant 500, the stent-graft portion can be merely a single walled stent-graft extending entirely down from the anchor portion of the implant 500, without any toroidal sections which require any filling. In this example the stent-graft is shown with dual tubes at lower ends extending into each of the iliac arteries IA. FIG. 40 again illustrates a cross-section where the stent-graft portion of the implant 500 is supported by thrombus T.

FIGS. 41-44 show a fifth example where an implant 600 in the form of custom stent-graft with renal artery anchor is provided according to this invention. In this example, a stent-graft with positioning anchor is custom manufactured to match the patient's particular geometry, in a situation where an aneurysm X exists both at the junction of the aorta with the renal arteries RA and with the aneurysm X extending below the junction with the renal arteries RA. Insufficient thrombus T exists to provide adequate support for the stent-graft portion extending below the anchor portion of the implant 600. Hence, a series of toroids are included on the stent-graft portion which can be separately filled with fixation media M similar to the inflation of the anchor portion of the implant 600.

Figure 42:
FIG. 42 is a front elevation view of a patient's anatomy in section showing the stent-graft with positioning anchor of FIG. 41 in full section implanted therein, and particularly showing how stents are utilized to hold arms of the anchor in position relative to renal arteries of the patient and with the double walled stent-graft extending from the anchor.
Figures 43, 44:
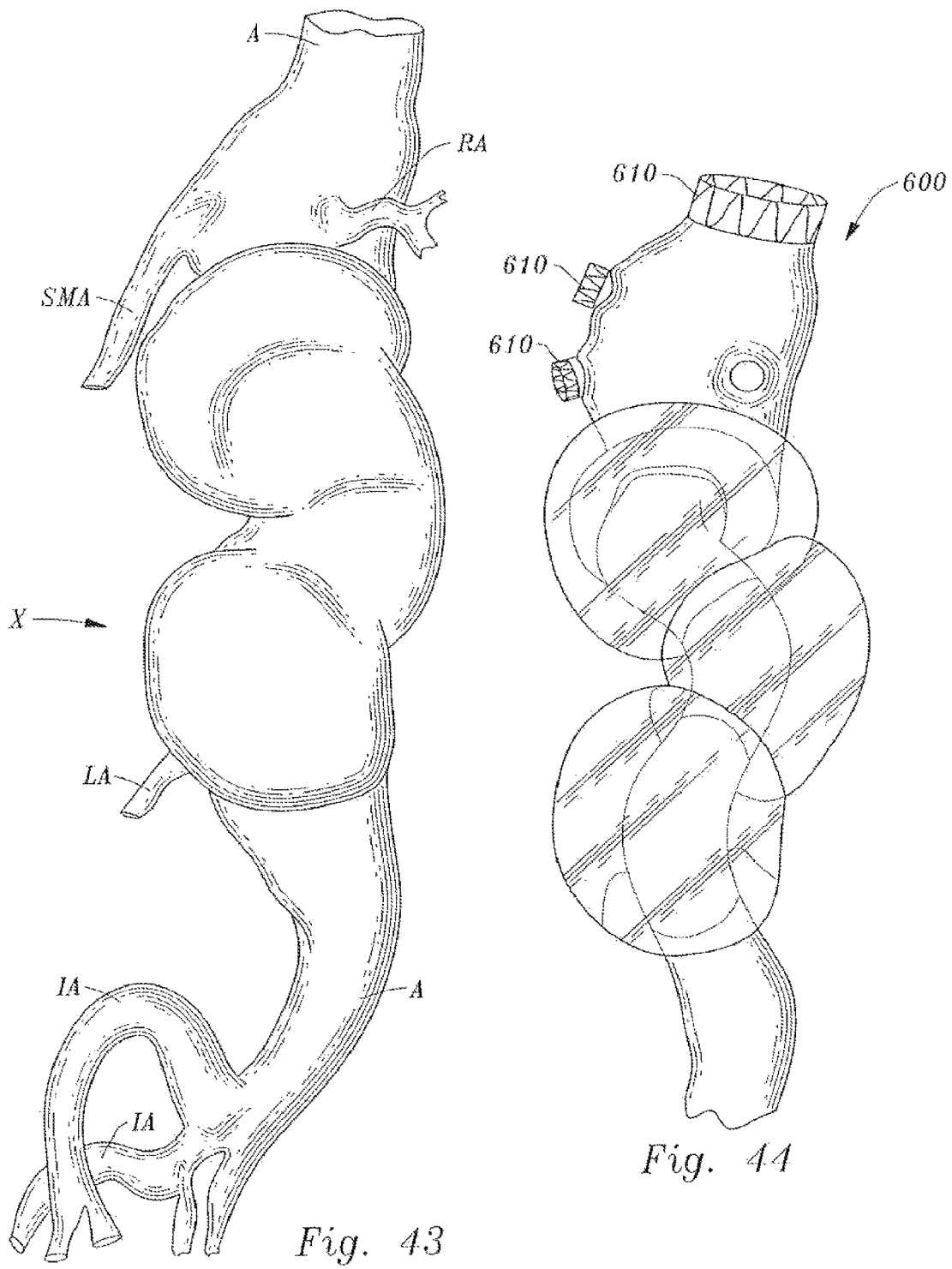
FIG. 43 is a side elevation view of the aorta of the patient shown in FIG. 42, and revealing how the superior messenteric artery is located relative to one of the renal arteries.
FIG. 44 is a perspective view of the stent-graft of FIG. 41 shown from a side so that the arms of the anchor positioned for insertion within the messenteric arteries are shown, and with radially expandable stents thereon for holding of the arms of the anchor in the desired positions, along with a stent for supporting an upper end of the anchor.

In FIG. 42 radially expandable stents 610 are shown to illustrate how the anchor portion of the implant 600 is held both within the renal arteries RA and within the aorta A (FIG. 42). FIG. 43 clearly illustrates the geometry of the aneurysm X from a side view with FIG. 44 showing the implant 600 from a side view to further illustrate the positioning of stents 610, particularly for use in holding the various arms of the anchor portion of the implant 600 within lateral arteries to secure the anchor portion of the implant 600 in the desired implantation position within the patient.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

The invention claimed is:

1. A catheter system for intraluminal delivery of an aneurysm treatment system, the catheter system comprising:
   a catheter having a proximal end and a distal end, the catheter having a delivery portion near the distal end, a balloon inflation fluid pathway extending from a proximal portion of the catheter to an expandable balloon on the delivery portion of the catheter, and a fixation medium delivery pathway extending from the proximal portion to the delivery portion; and
   an implantable double-walled filling structure disposed on the balloon and adapted for intraluminal placement at an intersection of a main vessel and at least two side branch vessel, the filling structure comprising an inner wall, an outer wall outside of an exterior of the inner wall, and a fillable void between the inner and outer wall,
   wherein, when deployed by filling the void with a fixation media delivered through the fixation medium delivery pathway, the inner wall surrounds and defines a primary fluid conduit having an upper and lower opening to facilitate blood flow across the intersection and further surrounds and defines at least two lateral fluid conduits extending laterally from and transverse to an axis of the primary fluid conduit, the at least two fluid conduits being in fluid communication with the primary fluid conduit between the upper and lower openings to facilitate blood flow from the primary fluid conduit through the at least two lateral fluid conduits into the at least two side branch vessels, and the outer wall conforms to an inside wall of the main vessel along the primary fluid conduit and to an inside wall of the at least two lateral fluid conduits along at least two arms of the filling structure extending into the at least two sidebranch vessels, each arm surrounding and defining a respective lateral fluid conduit, so as to substantially fill a space between an outside surface of the outer wall and the wall of each of the main vessel and the at least two side branch vessel at the intersection of the main and the at least two side branch vessels, wherein the fillable void between the inner and outer wall surrounds the primary fluid conduit and extends into each of the at least two arms in which the at least two lateral fluid conduits are defined and surrounds each lateral fluid conduit such that filling the fillable void expands the outer wall to contact the inside wall of each of the main vessel and the at least two sidebranch vessels when implanted within the main vessel and at least two side branch vessel.

2. The catheter system of claim 1, wherein the catheter further comprises a central conduit extending along the delivery portion of the catheter from a bypass inlet at one end of the deliver portion and a bypass outlet at an other end of the delivery portion so as to facilitate blood flow across the intersection during deployment of the filling structure.

3. The catheter system of claim 2, wherein the balloon is adapted to be expanded so as to substantially occlude a lumen in which the catheter is located such that blood flow through the intersection is directed through the central conduit during deployment.

4. The catheter system of claim 1, wherein the catheter is formed entirely of a material sufficiently flexible to allow the catheter to pass intraluminally from a femoral artery to an aorta of a patient.

5. The catheter system of claim 1, wherein at least a portion of the catheter and/or the balloon is formed of a radiopaque material.

6. The catheter system of claim 5 wherein the radiopaque material is selectively located at a plurality of positions axially and radially spaced from each other so that a position and orientation of the catheter system can be determined through fluoroscopy.

7. The catheter system of claim 1, further comprising:
   a sheath adapted to be slidably disposed over the filing structure collapsed on the balloon during delivery of the filling structure to the aneurysm.

8. The catheter system of claim 1, wherein the balloon comprises a lumen shaper balloon adapted to expand into an inflated form having a contour that at least partly matches a contour of the filling structure adjacent the at least two lateral fluid conduits of the at least two arms of the filling structure during deployment.

9. The catheter system of claim 8, wherein the lumen shaper balloon is adapted so that the contour positions the arm of the double-walled filling structure into the at least one sidebranch vessel during deployment.

10. The catheter system of claim 8, wherein the lumen shaper balloon is customized so as to match to a particular morphology of a patient.

11. The catheter system of claim 10, wherein the filling structure is customized so as to match to a particular morphology of a patient.

12. The catheter system of claim 1, further comprising:
one or more radially expandable stents adapted for deployment within the filling structure adjacent the upper and/or lower ends of the primary fluid conduit.

13. The catheter system of claim 1, further comprising:
one or more radially expandable stents adapted for deployment within each arm of the filling structure.

14. The catheter system of claim 1, wherein the double-walled filling structure comprises an anchor adapted for attachment to a graft, the graft having a tubular form surrounding a primary fluid conduit so as to extend the primary fluid conduit downstream of the anchor.

15. The catheter system of claim 14, wherein the graft is formed integrally with the anchor.

\* \* \* \* \*